US012758342B2

(12) United States Patent
Pouponneau et al.

(10) Patent No.: US 12,758,342 B2
(45) Date of Patent: Oct. 13, 2026

(54) SYSTEM AND METHOD FOR MOVING A MEDICAL DEVICE FOR TREATING OR DIAGNOSING A PATIENT

(71) Applicant: Artedrone, Paris (FR)

(72) Inventors: Pierre Pouponneau, Paris (FR); Ahmed Chah, Châteauroux (FR); Azaddien Zarrouk, Châteauroux (FR); Michel Grimaud, Versailles (FR); Karim Belharet, Châteauroux (FR)

(73) Assignee: Artedrone, Paris (FR)

( * ) Notice: Subject to any disclaimer, the term of this patent is extended or adjusted under 35 U.S.C. 154(b) by 601 days.

(21) Appl. No.: 18/262,108

(22) PCT Filed: Jan. 19, 2022

(86) PCT No.: PCT/EP2022/051114
§ 371 (c)(1),
(2) Date: Jul. 19, 2023

(87) PCT Pub. No.: WO2022/157189
PCT Pub. Date: Jul. 28, 2022

(65) Prior Publication Data
US 2023/0390013 A1 Dec. 7, 2023

(30) Foreign Application Priority Data
Jan. 21, 2021 (CH) .................................... 00058/21
Jul. 26, 2021 (EP) .................................... 21315129

(51) Int. Cl.
*A61B 34/00* (2016.01)
*A61B 34/30* (2016.01)
(Continued)

(52) U.S. Cl.
CPC ........ *A61B 34/73* (2016.02); *A61B 2034/303* (2016.02); *A61B 2034/731* (2016.02); *A61B 2090/064* (2016.02); *A61M 25/0127* (2013.01)

(58) Field of Classification Search
CPC .............. A61B 34/73; A61B 2034/303; A61B 2034/731; A61B 2090/064; A61B 90/39;
(Continued)

(56) References Cited

U.S. PATENT DOCUMENTS 5,125,888 A * 6/1992 Howard ............ A61M 25/0105 604/890.1
2004/0030244 A1* 2/2004 Garibaldi ............... A61B 5/062 600/117
2009/0076539 A1 3/2009 Rentschler et al.
2013/0282173 A1 10/2013 Gunday et al.
2017/0189654 A1* 7/2017 Schwartz ............ A61M 5/1723
2020/0342985 A1* 10/2020 Toth ....................... A61B 5/308

FOREIGN PATENT DOCUMENTS

EP 3 782 543 A1 2/2021
KR 10-2019-0101190 A 8/2019
(Continued)

OTHER PUBLICATIONS

Ke Meng, "Motion Planning and Robust Control form the Endovascular Navigation of a Microrobot", (Jul. 2020), IEEE Transactions on Industrial Informatics, vol. 16, No. 7, pp. 4557-4566 (Year: 2020).*
(Continued)

*Primary Examiner* — Kaitlyn E Sebastian
(74) *Attorney, Agent, or Firm* — Secant IP, P.L.L.C.

(57) ABSTRACT

A system (10) for moving an intravascular medical device (85) in a vascular network (V) comprises a magnetic actuator (40), a controlling unit (50) and a controlling line driver (60). The controlling line driver (60) is adapted to hold and/or to release a controlling line (70) attached to the medical device (85) at different speeds. The magnetic actua-
(Continued)

Figure 1A:
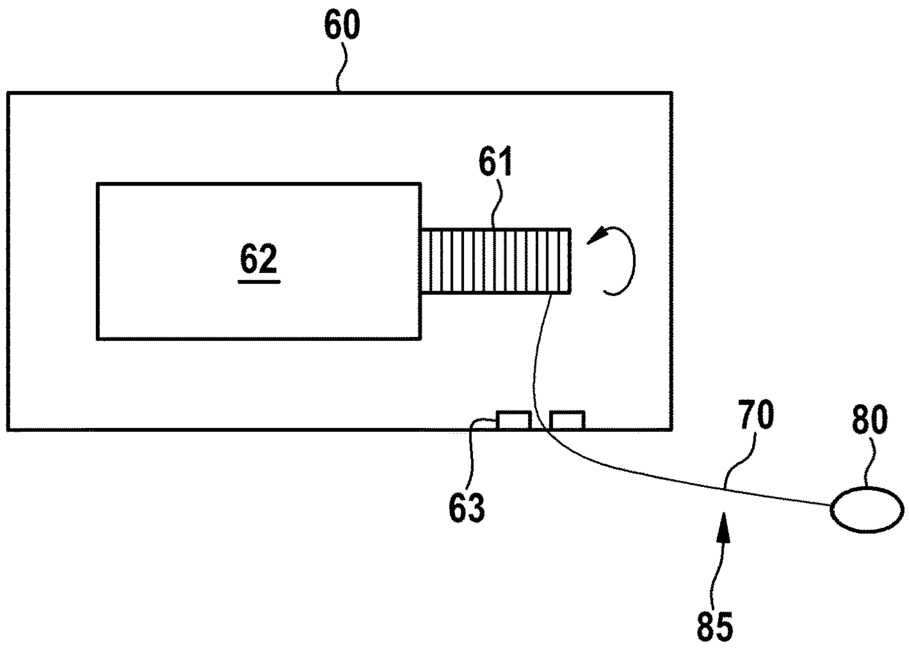

tor is adapted to generate a magnetic field (41) at a predetermined location in order to pull the medical device (85) in a pre-determined direction. The controlling unit (50) is adapted to balance at least three forces applied on the medical device (85) and to operate the magnetic actuator (40) and/or the controlling line driver (60).

16 Claims, 15 Drawing Sheets

(51) Int. Cl.
*A61B 90/00* (2016.01)
*A61M 25/01* (2006.01)

(58) Field of Classification Search
CPC ...... A61B 2034/2065; A61B 2090/374; A61B 2090/376; A61B 2090/3762; A61B 2090/378; A61B 34/30; A61B 34/32; A61B 34/71; A61B 90/37; A61B 34/25; A61B 34/20; A61B 2017/00345; A61M 25/0127
See application file for complete search history.

(56) References Cited

FOREIGN PATENT DOCUMENTS

| | | | | |
|---|---|---|---|---|
| WO | 2020/064663 A1 | | 4/2020 | |
| WO | WO-2021009615 A1 | * | 1/2021 | ........ A61M 25/0158 |

OTHER PUBLICATIONS

L. Pancaldi et al., "Flow driven robotic navigation of microengineered endovascular probes", Nature Communications, 11, Article No. 6356, Dec. 22, 2020, See Spc. p. 1.

K. Meng et al., "Motion Planning and Robust Control for the Endovascular Navigation of a Microrobot", IEEE Transactions on INdustrial Informatics, vol. 16, No. 7, Jul. 2020, pp. 4567-4566, See International Search.

L. Arcese et al., "Endovascular Magnetically Guided Robots: Navigation Modeling and Optimization", IEEE Transactions of Biomedical Engineering, vol. 59, No. 4, Apr. 2012, pp. 977-987, See International Search.

International Search Report Corresponding to PCT/EP2022/051114 mailed Apr. 12, 2022.

Written Opinion Corresponding to PCT/EP2022/051114 mailed Apr. 12, 2022.

* cited by examiner

SYSTEM AND METHOD FOR MOVING A MEDICAL DEVICE FOR TREATING OR DIAGNOSING A PATIENT

The present invention relates to a system for moving a medical device in a vascular network and a method of treating or diagnosing a patient according to the preamble of the independent claims.

It is generally known in the prior art to use devices inside a human body to perform certain treatments.

For example, US 2009/0076536 A1 discloses microrobots or devices that can be introduced into a human body and perform medical treatments, in particular to provide spatial support in a cavity.

US 2013/0282173 A1 discloses remote-controlled surgical robots that can move within a patient's body and perform medical actions therein.

WO 2020/064663 discloses a medical device with a recapture line.

Pancaldi et al. (Nat. Commun. 11, 6356 (2020)) discloses tethered endovascular microscopic probes for transported through vascular networks, using hydrokinetic energy. Using magnetic actuation, a probe head may be deformed in order to achieve dynamic steering.

However, known devices have several drawbacks. In particular, reliable navigation in a vascular network may be difficult to achieve, especially in tortuous vascular networks. The magnetic navigation of a medical device pushed by the flow through several bifurcations is challenging because the magnetic field has to be set for each bifurcation. In the case of high flow, the magnetic field of the system may not be strong enough to change the device direction. Moreover, the automated magnetic navigation through successive bifurcations requires to control the medical device position and the magnetic actuator.

Thus, the object of the present invention is to overcome the drawbacks of the prior art, in particular to provide a simple and reliable means of navigating a medical device in a vascular network. In particular, the system and method aim at automating and/or optimizing a magnetic device guidance.

These and other objects are achieved by the system and the method according to the characterizing portion of the independent claims of the invention.

The system according to the invention is particularly suited for moving a medical device in a vascular network. The medical device may, in particular, be an implantable device. The medical device may comprise a head section with a magnetic part and a back section with a controlling line. The medical device can be moved in the vascular network in order to treat or diagnose a patient. The system comprises a magnetic actuator, a controlling unit and a controlling line driver. The controlling line may be attached to the controlling line driver. The controlling line driver, when said controlling line it attached to the controlling line driver, is adapted to hold and/or release a controlling line at different speeds. The magnetic actuator is adapted to generate a magnetic field at a predetermined location. Preferably, the magnetic field is predetermined. The magnetic field may exert a force on the medical device, in particular the magnetic part of the medical device, such as to pull the medical device in a predetermined direction. The controlling unit is adapted to balance at least three forces applied on the medical device. Preferably, the controlling unit balances the forces in real time. Preferably, the three forces include at least one of a drag force acting on the medical device by a fluid flow, for example blood in a vessel, a force by the controlling line, and a magnetic force by the magnetic actuator. The controlling line further operates the magnetic actuator and/or the controlling line driver.

The controlling line can help with the magnetic navigation. The present invention helps to find a good equilibrium on the different forces applied on the medical device: flow force, gravity force, controlling force and the magnetic force or other potential forces acting on the medical device in order to navigate the medical device along the trajectory path. The system can automatically compute the forces and the relations between the forces and define the forces generated by the system, especially the controlling line force and the magnetic force, to ensure that the resulting force moves the medical device along a predefined trajectory.

This balancing model allows also to optimize the distribution of forces induced by the magnetic actuator and the controlling line. The balancing of forces may also be beneficial for optimizing system requirements, such as e.g. lower magnetic fields and/or lower controlling line forces.

The controlling line driver may comprise, preferably consist of, any one of or a combination of a pulley, a linear actuator, a reel, an electric motor, a spindle, a gear, a screw and/or a nut, a linear gear track, and a continuous track. The controlling line driver may also comprise two or more of any one of these elements, also in combination with any one, two, or more of any other element.

The controlling line driver may also comprise, additionally or alternatively, a controlling line connector adapted for providing an operable connection between the controlling line driver and the controlling line.

Preferably, the controlling unit may comprise a processor and/or a memory. In a particularly preferred embodiment, the controlling unit is in operable connection with an electric motor and is adapted to control at least one of speed, power, and torque of the electric motor.

The speed may be at least partially predetermined, automatically determined or manually chosen. It is conceivable to use a combination of predetermined, automatically determined, and manually chosen speeds. For example, the controlling unit may calculate a suitable speed profile based on a planned trajectory in a vessel taking into account data about the flow of blood in said vessel and save the speed profile in a memory. Additionally or alternatively, the speed of the controlling line may be adapted during an intervention automatically, for example via feedback loop taking into account a planned trajectory and actual position data, and/or manually by a user. To this end, the system may preferably comprise an interface for a user, for example one or more touch screens, knobs, buttons, levers, adapted for allowing input of speed parameters. It is possible to use the same or additional interfaces for inputting further parameters related to control of position and speed of the medical device.

Preferably, the controlling unit is adapted to calculate a magnetic field at a device position in space and/or a force exerted on a magnetic element by said magnetic field when the magnetic element is positioned at the device position in space. The controlling unit may in particular take into account at least one of a position, an orientation, and/or a power of the magnetic actuator. Additionally or alternatively, the controlling unit may be adapted for receiving data from a sensor at or close to the device position, in particular data related to the magnetic field and/or force at the device position.

Additionally or alternatively, the device may calculate at least one of a position, an orientation, and a power of the magnetic actuator suitable to achieve a magnetic field and/or a magnetic force at the device position. The magnetic field and/or magnetic force may be calculated qualitatively (e.g. only a direction) or quantitatively.

It is conceivable that the controlling unit is adapted to perform a closed feedback loop with respect to magnetic actuator, i.e. to calculate the position, orientation and/or power of the magnetic actuator based on a desired force and/or magnetic field, and to adapt or correct said position, orientation and/or power, for example based on an actual measured field and/or force.

The controlling unit may further be adapted to calculate and/or determine a force acting on the medical device through the controlling line. To this end, the controlling unit may comprise and/or be in operable connection with a force sensor adapted to to measure a force acting on the medical device. The controlling unit may control the controlling line driver such as to release the controlling line while keeping a force acting on the medical device via the controlling line constant. Additionally or alternatively, the controlling unit may be adapted to control the controlling line driver such as to release the controlling line at a constant speed. Yet additionally or alternatively, the controlling unit may be adapted to control the controlling line driver such as to release to controlling line at a speed and/or with a pull-back force that is determined based on a magnetic force acting on the medical device.

Particularly preferably, the controlling unit may control and/or limit, via the controlling line driver, one of the speed and position of the medical device via the controlling line.

The controlling unit may further calculate and/or determine a drag force acting on the medical device due to a surrounding blood flow. The system may comprise a sensor adapted to measure a blood flow velocity at the device position, for example a Doppler ultrasound device. Additionally or alternatively, force data provided by the force sensor may be taken into account. Additionally or alternatively, the system may comprise a memory device containing flow data acquired before or during a treatment in dependence of a position in a vessel.

Thus, the controlling unit is adapted to balance three forces that may be acting on the medical device. Balancing of a number of forces may in particular be understood as adapting the magnitude of at least one force in response and/or based on at least one other force, preferably all other force, of the number of forces.

The controlling unit may be adapted to increase or reduce the magnetic force acting on the medical device by adapting at least one of the position, orientation and/or power of the magnetic actuator depending on the force exerted on the medical device by the blood flow and/or the controlling line. For example, if a force exerted on the medical device by the blood flow is too low for the medical device to move along a longitudinal axis of the vessel, the controlling unit may adapt the operation of the magnetic actuator such as to at least partially exert a force in a direction substantially parallel to the longitudinal axis such as to propel the medical device forward.

Additionally or alternatively, the controlling unit may be adapted to increase or decrease the velocity of the release of the controlling line depending on the drag force exerted on the medical device by the blood flow and/or the magnetic force exerted on the medical device by the magnetic actuator. For example, the controlling unit may determine that the magnetic force that is available may be limited due to space constraints or distance between a tissue and the magnetic actuator and/or the drag force exerted by blood flow strong enough such that the available magnetic force is not sufficient to move the medical device in an intended direction. Thus, the controlling unit may operate the controlling line driver to slow down and/or stop the release of the controlling line such as to slow down and/or stop the medical device. As a consequence, a smaller magnetic force may be sufficient to move the medical device in a desired direction because the medical device has a lower speed, in particular compared to the surrounding blood flow.

The system may comprise orientation means to orient the magnetic field. The orientation means may be in operable connection with the controlling unit. For fields generated by permanent magnets, the orientation may be performed by moving the magnetic actuator, in particular by using orientation means having arms, joints, telescopes, wheels, gears, rails, and others and combinations thereof. In particular, the orientations means may comprise a robotic arm with six degrees of freedom for moving a permanent magnet.

In case of a field generated by a non-permanent magnet, the orientation of the magnetic field can be accomplished by changing the current of the electro-magnets and/or by using orientations means as described for a permanent magnet.

In one embodiment according to the invention, the system is additionally or alternatively intended for treating or diagnosing a patient by using a, preferably implantable, medical device having a magnetic part and a shape, size and surface structure defining a movement component of the medical device when it is dragged by a bodily fluid. The system comprises a magnetic actuator, a controlling unit and a controlling line driver. The controlling line may be attached to the controlling line driver. The controlling line driver is or can be brought in operable connection with the controlling unit such that at least one of the position, a movement and a velocity along the axis of a controlling line when attached to the controlling line driver is controllable by the control unit via the controlling line driver. Additionally or alternatively, the controlling unit may be adapted to at least partially control the position and/or the velocity of the medical device, when in operable connection with the controlling unit via the controlling line attached to the controlling line driver, within a vessel via at least one of the position, the velocity and the movement of the controlling line driver.

The controlling unit may further be adapted to control a position of the medical device within the vessel, preferably in a plane perpendicular and/or in a direction parallel to a longitudinal axis of the vessel, via the magnetic actuator. Preferably, the controlling unit is adapted to take into consideration the drag force exerted on the medical device by the blood flow for actuating the magnetic actuator and/or for controlling the movement or position of the controlling line. Additionally or alternatively, the controlling unit may further be adapted to actuate the magnetic actuator based on the velocity of the controlling line or to adapt the velocity of the controlling line based on the magnetic field generated by the magnetic actuator. Particularly preferably, the controlling unit is adapted to determine three force components exerted on the medical device by blood flow, magnetic forces and the controlling line respectively and to control the controlling line driver and the magnetic actuator such as to balance the three force components in order to achieve an intended movement of the medical device.

The system may preferably comprise a medical device having a magnetic part and a shape, size and surface structure defining a movement component of the medical device when it is dragged by a bodily fluid.

Preferably, the medical device is a microrobot adapted to perform a function within the patient. The microrobot may, for example, remove tissue mechanically, release a drug, provide heat or cold, induce thrombosis and/or remove a thrombus.

Particularly preferably, the medical device comprises at least a first surface portion configured to maximize a drag force in aqueous media, in particular in blood. The surface portion may be arranged at least partially circumferentially of the medical device, in particular in a plane perpendicular to a longitudinal axis defined by the line. Thus, forward propulsion by blood, i.e. the drag force, may be maximized. It may, additionally or alternatively, be advantageous to include a second surface portion, in particular arranged at a tip/intersecting with the longitudinal axis defined by the controlling line, that minimizes a friction force with the aqueous medium in order to reduce the magnetic force necessary for guiding.

Preferably, a density of the medical device head section and/or the controlling line, particularly preferably the density of the medical device as a whole, is substantially identical to the density of water or blood, in particular water or blood at physiological conditions (i.e. at 37° C. and physiological salt concentration). Thus, the medical device may be navigated in a blood vessel without the need to take into account a gravitational force.

Additionally or alternatively, the system may further comprise a controlling line. The controlling line may be connected or connectable to the controlling line driver in order to be brought in operable connection with the controlling unit.

Particularly preferably, the controlling line is connected or connectable to the head section of the medical device.

In some embodiments, the controlling line driver may be adapted for controlled release, in particular with controlled velocity and/or controlled force, of the controlling line. Particularly preferably, the controlling line driver may be adapted to pull the controlling line back. To this end, the controlling line may be adapted, in particular by material choice and/or dimensioning and/or structure, to have a strength, in particular a tensile strength or yield strength, that is sufficient to withstand the drag force induced by blood flow on the medical device when it is moved in a direction opposite of the blood flow.

The system according to any one of the preceding claims, wherein the system has a detection component which is adapted to detect a bifurcation in a vessel system. For example, the detection component may comprise an image analysis software and/or an interface for receiving imaging data. Additionally or alternatively, the system may comprise data representative of the location and orientation of bifurcations in a memory, wherein the detection component is adapted to read such data via an interface.

Preferably, the system is configured to determine, based on a current velocity of the medical device and the distance between the medical device, in particular the medical device head section, and the bifurcation along a flow direction within the vessel, a minimum magnetic force necessary for displacing the medical device such as to guide the magnetic device at the bifurcation.

Preferably, the magnetic actuator comprises at least one of an electromagnet and a permanent magnet. The magnetic actuator may create a magnetic field with a gradient. Electromagnets are particularly advantageous because they provide an electrically tunable magnetic field.

The system according to the invention thus allows for easy and reliable navigation in a vessel. In particular, for guiding, navigating or steering the medical device, the system does not necessarily require a shape change, such as bending, of the medical device (and in particular of its head portion) in response to a magnetic actuation. Instead, the system allows for magnetic actuation to be tuned independently of flow properties. For example, a medical device may still be navigated in a vessel if blood flow is virtually zero or very fast. Furthermore, the system may allow for higher flexibility in magnetic actuation devices and their operation, as a resulting force exerted by the magnetic field is used without relying on a shape changes to achieve changes in direction of the by harnessing hydrokinetic energy. As such, it may not be necessary to achieve a particular orientation of a magnetic field with respect to the medical device and in particular the medical device head section. However, it will be understood that medical devices that are adapted to change a shape in response to a magnetic actuation may be combined with the system according to the invention.

Furthermore, the system according to the invention is more reliable because the additional control of the position and velocity of the medical device by means of the controlling line allows for longer reaction times, making the procedure less error-prone. In addition, the controlling line may be used for, manual or automatic, at least partial retraction of the medical device, allowing for simple correction of a navigation path.

Due to the limitation of the velocity of the medical device that can be achieved by means of the controlling line, weaker magnetic forces/magnetic fields may be employed for navigation. Thus, both space and energy requirements may be reduced, leading to cheaper and simpler treatment options. In addition, strong magnetic fields that are typically required by devices already known in the art may not be suitable for patients with certain types of implants, such as pacemakers.

In particular, the magnetic force and thus the weight of the magnetic actuator necessary for actuation in a fluid typically increases with the flow velocity of the fluid. By contrast, slowing down and/or stopping the medical device can allow to use a constant and/or lower magnetic force to actuate the medical device independent of the fluid flow velocity and may thus reduce the total weight of the magnetic actuator and system.

Thus, preferably, the magnetic actuator is configured such as to create a magnetic force not sufficient to move the medical device against the flow of blood. The magnetic actuator may in particular be a permanent magnet or electromagnet dimensioned accordingly. Magnetic actuators that only provide limited magnetic field strength may be smaller, cheaper, and safer for the patient.

Preferably, the controlling unit is adapted to balance at least four forces applied on the medical device. One of the at least four forces may be a gravitational force or a contact force, preferably of the medical device head section and/or the controlling line, with the blood vessel wall.

To this end, the controlling unit may further be adapted to compute the gravitational force from the properties and position of the medical device and/or to detect, for example based on imaging data, an orientation of the movement of the medical device and/or whether or not the medical device head section and/or the controlling line is in contact with a vessel wall. Particularly preferably, the controlling unit may be adapted to calculate quantitatively at least one of a force acting on the medical device due to contact of the medical device head section and/or the controlling line with the vessel. Additionally or alternatively, the controlling unit may be adapted to receive data from a sensor that measures a contact force acting on the medical device.

Preferably, the controlling unit is adapted to take into account a friction force between the controlling line and the blood vessel wall.

The controlling unit may determine the friction force in any manner described above, e.g. from imaging data, in particular three-dimensional imaging data. The controlling unit may also calculate the friction force based on data stored in the memory. For example, an average or normalized frictional force component may be stored and/or computed and used alone or in combination with imaging data. Additionally or alternatively, the system may comprise a sensor adapted to measure a frictional force and an interface to provide frictional force data to the controlling unit, preferably via the memory.

Preferably, the controlling unit is adapted to balance the contact forces induced by the head section with the blood vessel wall, in particular a friction force, an adhesion force and a penetration force.

Preferably, data representing at least one of the friction force, adhesion force and penetration force is stored in a memory, wherein the controlling unit is adapted to access these data via an interface. The different forces—friction, adhesion, penetration—can be computed from numerical models which may be stored on a storage accessible by the system. These numerical models can use vascular geometrical data, in particular extracted from pre-op and/or peri-op images.

Preferably, the system comprises at least two magnetic actuators. The controlling unit is preferably adapted to control the at least two magnetic actuators.

Two or more magnetic actuators may provide for more precise tuning of a magnetic force, in particular if only weak magnetic forces are employed. Furthermore, multiple magnetic actuators may allow for more flexibility in guiding a medical device and enable guiding in directions that may otherwise not be accessible due to space constraints limiting the movement of the magnetic actuator.

Preferably, the controlling unit comprises at least one of an imaging system and an interface for receiving intra-operative data from an imaging system, preferably an input interface for receiving imaging data. The controlling unit may be adapted to locate the position of the medical device, in particular of the medical device head section.

The imaging system may be any imaging device known in the art, in particular interventional systems such as Cath Lab, ultrasound imaging systems, magnetic resonance devices, fluoroscopy, X-ray imaging devices, and/or computer tomography.

Preferably, the controlling unit detects the position of the medical device by means of a locating element arranged with respect to the medical device.

Additionally or alternatively, the controlling unit may comprise an image analysis software adapted to detect the position of the medical devices on generated imaging data.

The controlling unit may store positioning data in the memory, in particular for calculating magnetic and drag forces as described above.

Preferably, the controlling unit is adapted to compute at least one force, in particular any of the above-mentioned forces, based on trajectory data that are representative for predetermined vascular path.

Preferably, the controlling unit comprises an interface for the user to enter the trajectory data, wherein the trajectory data is stored in the memory.

Preferably, the controlling unit is adapted to control the controlling line driver to slow down and/or stop the displacement of the medical device when moving at least one magnetic actuator to a next position.

In particular when subsequent bifurcations are located close to one another, slowing down and/or stopping the medical device may provide more time to accurately position the magnetic actuator.

In addition, depending on the patient's anatomy and the location of bifurcations along a planned trajectory, it may not be possible to move the magnetic actuator directly to the next position without moving the medical device in an unintended direction. In such cases, stopping the medical device may allow movement of the magnetic actuator without unintentionally propelling the medical device forward. Similarly, the additional time gained by slowing down and/or stopping the medical device may allow for moving the magnetic actuator away if necessary, i.e. to avoid positions wherein the medical device is moved in an unintended direction.

Additionally or alternatively, the system may be configured to stop the movement of the medical device with respect to the bifurcation at an upstream position of the bifurcation.

Preferably, the controlling line driver comprises a force sensor. The sensor may be adapted to measure a drag force exerted on the medical device by blood or another medium. The force sensor may functionally be arranged between the controlling line and the controlling line driver and form at least partially an interface for connecting the controlling line driver and the controlling line.

The force sensor may be any force sensor known in the art, in particular a piezo sensor, a spring sensor, a torque sensor, a capacitor, or others.

The force sensor may provide real-time force data, for example of a force exerted on the controlling line by contact to a vessel wall or blood flow.

Additionally or alternatively, the system may comprise a further force sensor not part of the controlling line driver. For example, the force sensor may be arranged at or form part of the medical device, an interface between the medical device head section and the controlling line, or at other locations.

Preferably, the controlling line drive comprises at least one interface to trigger and/or power at least one function of the medical device.

The controlling line driver may comprise a power source, such as an electrical plug, a battery, or any other power source known in the art. Additionally or alternatively, the controlling line driver may be adapted to transmit power wirelessly to the medical device. For example, radio-frequency identification (RFID) technology could be used to power the medical device.

The controlling line driver preferably has a size, shape and material so that it can be connected at the patient side. In particular, the controlling line driver may be adapted to be used in a sterile environment.

The controlling line may be preferably embedded into a sterilized feature. A sterile feature is a physical element protecting the controlling line driver from being in contact with nonsterile elements. A sterile feature can be a bag, a box. In one embodiment, the controlling line support and the controlling line are embedded into a sterile feature.

The sterile feature of the controlling line driver can be filled with a sterile solution, especially an isotonic solution.

Preferably, the system comprises multiple controlling line drivers, preferably two, three, or four controlling line drivers.

The controlling unit may be adapted to operate the magnetic actuator and the multiple controlling line drivers to control the navigation of multiple medical devices, particularly preferably wherein one medical device is attachable or attached to one controlling line driver each.

In a preferred embodiment, the system further comprises a flow member adapted to accelerate or slow down blood flow at least in the vicinity of the medical device. For example, the flow member may compress or enlarge a vessel mechanically or via release of a drug, locally increase or decrease a blood pressure, or locally restrict or enlarge a cross-section of the vessel.

The system may preferably comprise means for controlling and/or reducing and/or increasing the blood flow in a vessel. Particularly preferably, a balloon attached to a delivery catheter and a separate catheter is used. It is also conceivable, however, to use an external device, for example a compression device.

It will be understood that a local change in the flow may lead to changes in the flow direction and/or intensity in a different, possibly remote and/or distal, area.

It will be understood that the means for controlling and/or reducing blood flow may be attached or attachable to any part of the medical device and/or delivery catheter. Alternatively, the means may be configured as a separate device.

Reducing or increasing the blood flow in a particular vessel can be advantageous and provide better control over navigation.

The system may further comprise at least two controlling line drivers. Each controlling line driver may be independently controllable by the controlling unit. One controlling line may be attached or attachable to each controlling line driver and may thus be controlled independently.

Such a configuration allows to additionally steer and/or rotate the medical device using the controlling lines, when the at least two controlling lines are attached to the same medical device.

It will be understood, however, that the at least two controlling line drivers may also be used to independently control the motion of at least two separate medical devices.

The invention is further directed to a method of treating or diagnosing a patient. Preferably, the method is performed using a system as described herein. The method comprises the steps of:

- introducing a medical device in a vessel of a patient.
- Computing balanced forces applied on the medical device to create a resulting force, wherein the resulting force is able to move the medical device along a predetermined path.
- Operate at least one magnetic actuator, preferably via a controlling unit, to create at least one magnetic field at at least one pre-determined location.
- Adapting the releasing velocity of a controlling line attached to the medical device head section.

Preferably, an optimal path to a targeted area is calculated by the controlling unit. Alternatively, data representing an optimal or desired path determined by a user may be entered into a memory via an interface.

Preferably, the method further comprises a step of moving the medical device along a predetermined path.

Preferably, the method comprises the further step of stopping the medical device prior to a bifurcation.

Additionally or alternatively, the method may further comprise any one of the following steps, or any combination thereof:

- Moving the medical device in a direction substantially identical with the direction of a flow of blood within the vessel substantially solely by a drag force exerted by the flow of blood;
- Controlling the velocity of the medical device by exerting a force on a controlling line connected to the medical device head section, wherein the force is preferably directed in a direction opposite the direction of the flow of blood within the vessel;
- Detecting a bifurcation in the vessel;
- Reducing the velocity of medical device, preferably stopping the medical device, at an upstream position of the bifurcation by controlling the controlling line;
- By means of a magnetic actuator, moving the medical device in a direction perpendicular to a longitudinal axis of the vessel such as to guide the medical device toward a branch of the bifurcation
- Preferably releasing the line in order to accelerate the medical device by means of the drag force exerted by the flow of blood.

The invention is further directed to a-a medical device, preferably a microrobot. The medical device is particularly suitable for use with a system as described above and/or in a method as described above. It will be understood that the medical device may have any of the features described in the context of the system herein. The medical device may comprise a magnetic part which can be brought in operable connection with the magnetic actuator, and preferably at least a surface portion adapted to maximize a drag force in an aqueous medium, in particular blood. A medical device head section is connected or connectable to a controlling line.

Figure 5:
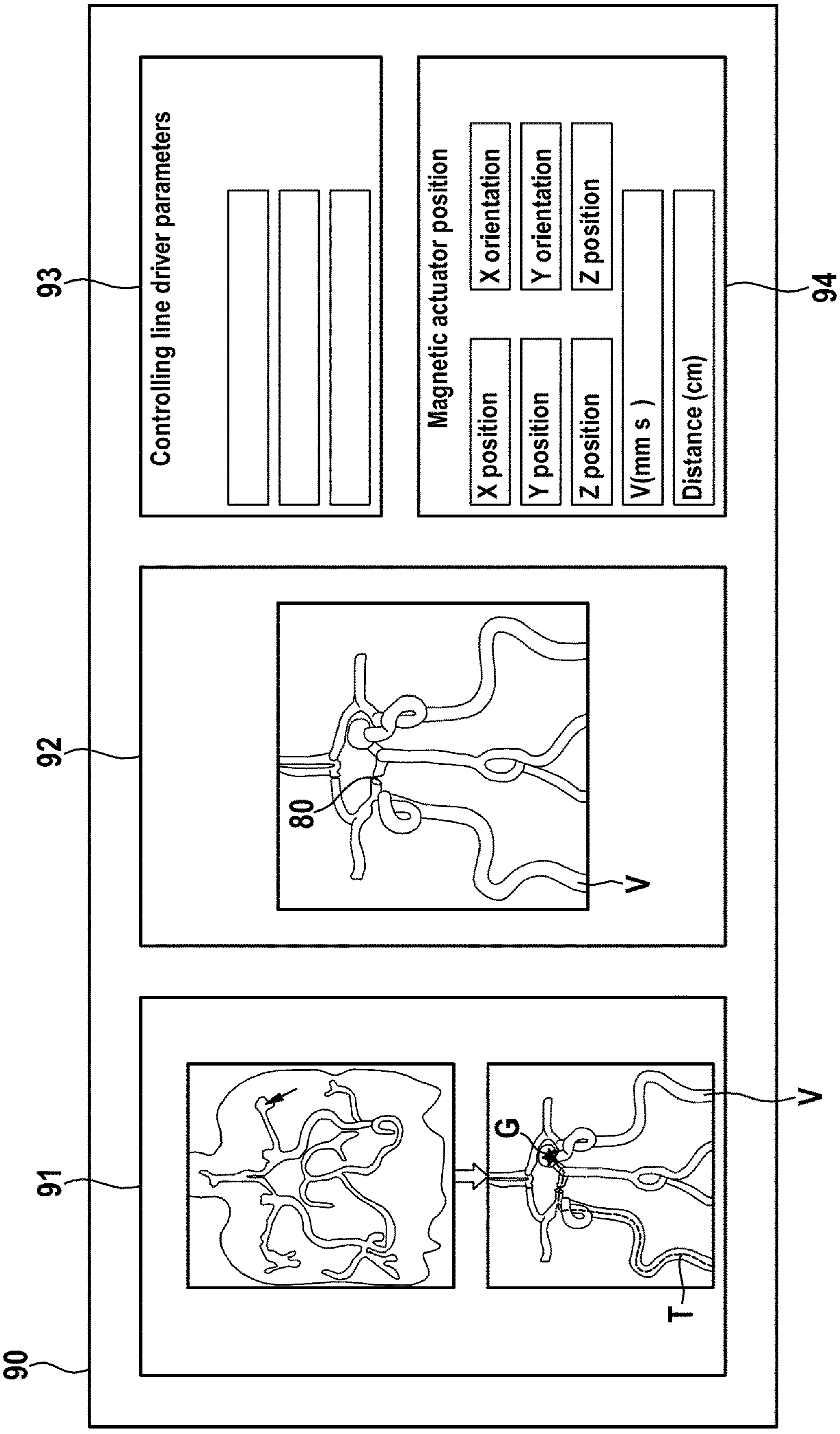
Figure 6:
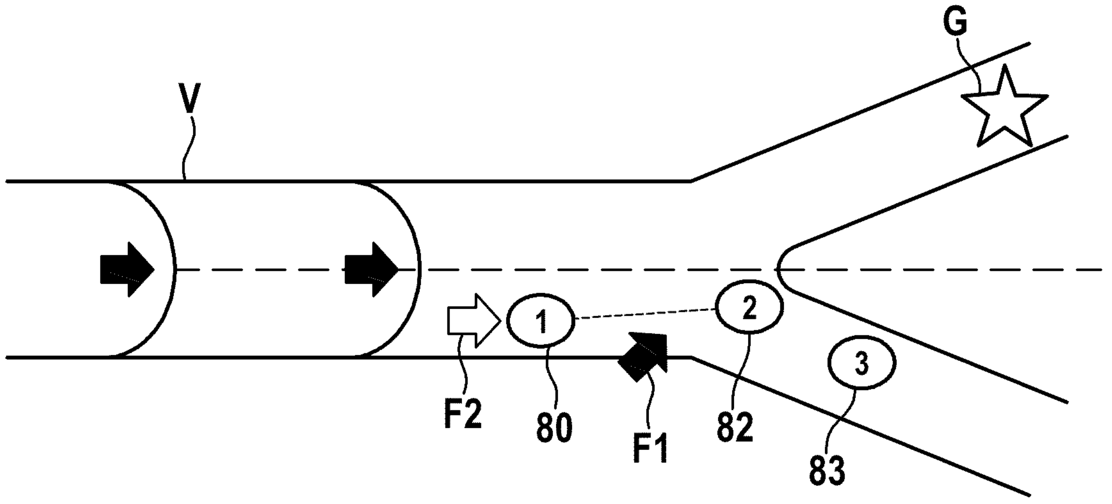
Figure 7:
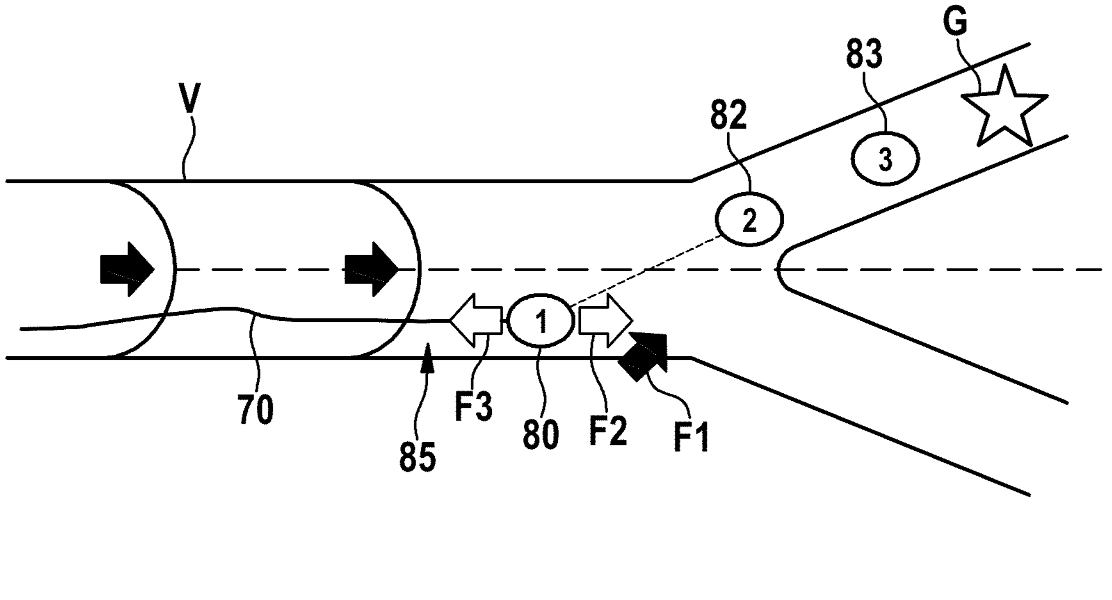
Figure 8:
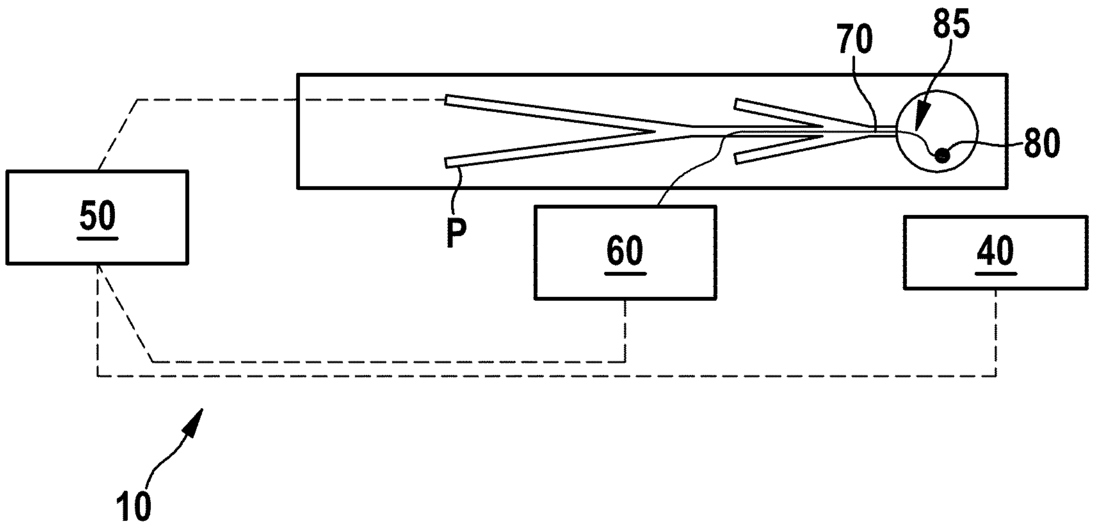
Figure 9:
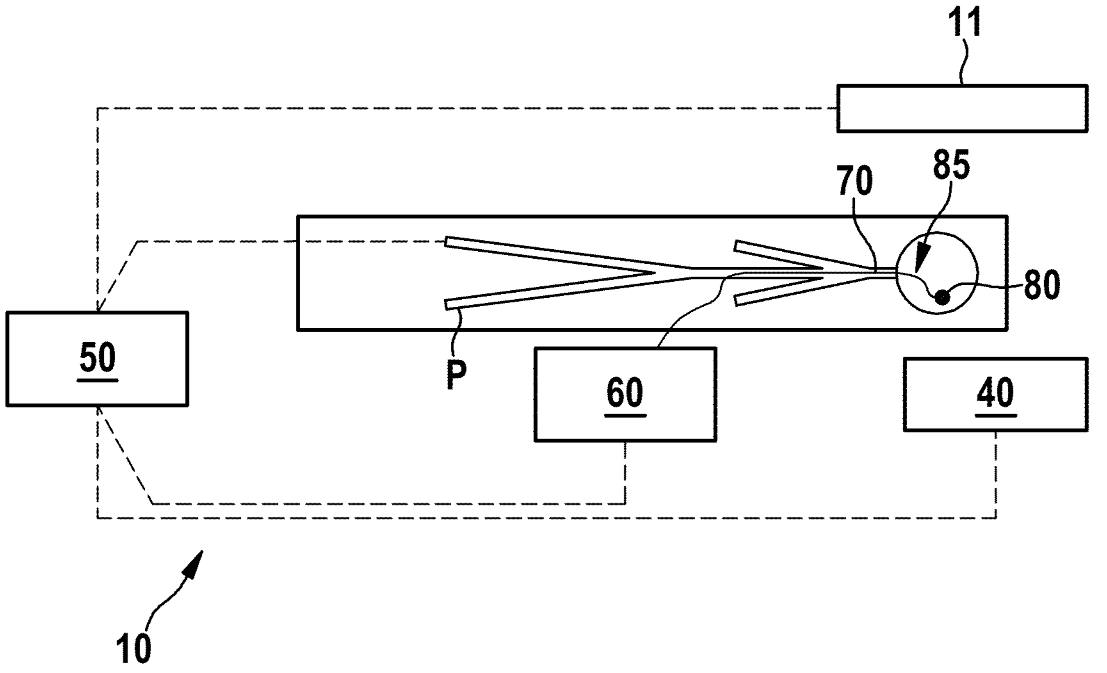
Figures 10A, 10B, 10C:
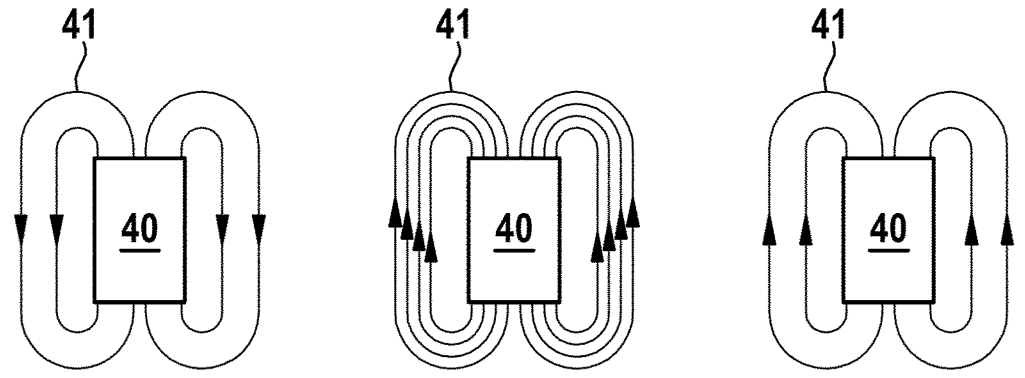
Figure 11:
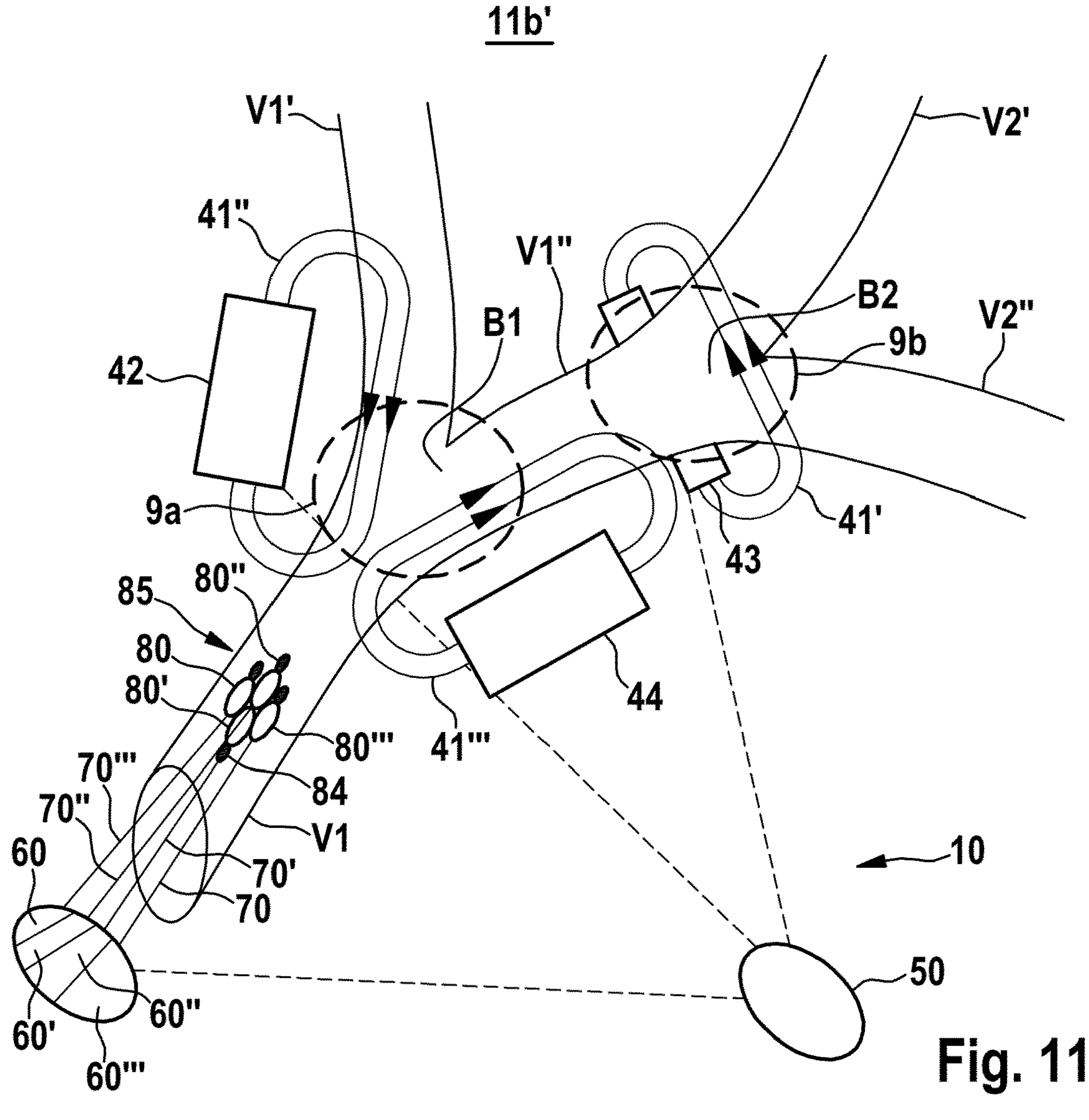
Figure 12:
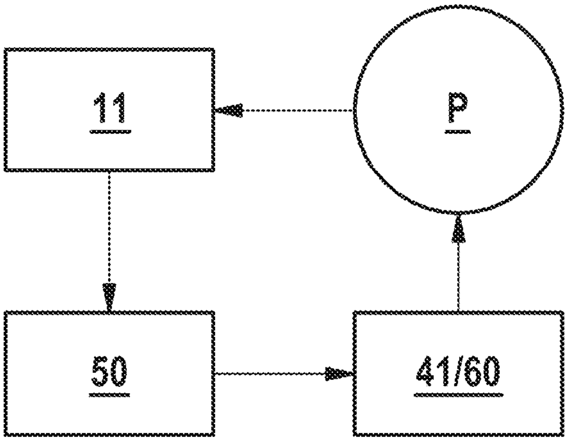

In the following, the invention is described in detail with reference to the following figures, showing:

FIG. 1*a*-1*d*: a first embodiment of a controlling line driver in use;

FIG. 2 *a*-2 *b*: a second embodiment of a controlling line driver;

FIG. 3 *a*-3 *b*: a third embodiment of a controlling line driver;

FIG. 4 *a*-4 *b*: a fourth embodiment of a controlling line driver;

FIG. 5: schematically a user interface of a controlling unit;

FIG. 6: a medical device being navigated in a vessel of a patient;

FIG. 7: a medical device being navigated in a vessel by a system for moving a medical device;

FIG. 8: a first embodiment of a system for moving a medical device;

FIG. 9: a second embodiment of a system for moving a medical device;

FIGS. 10*a*-10*c*: a schematic illustration of a magnetic actuator;

FIG. 11: a schematic illustration of multiple medical devices being moved in a vessel by a system for moving a medical device;

FIG. 12: a schematic illustration of the working principle of the actuation device.

Figure 13:
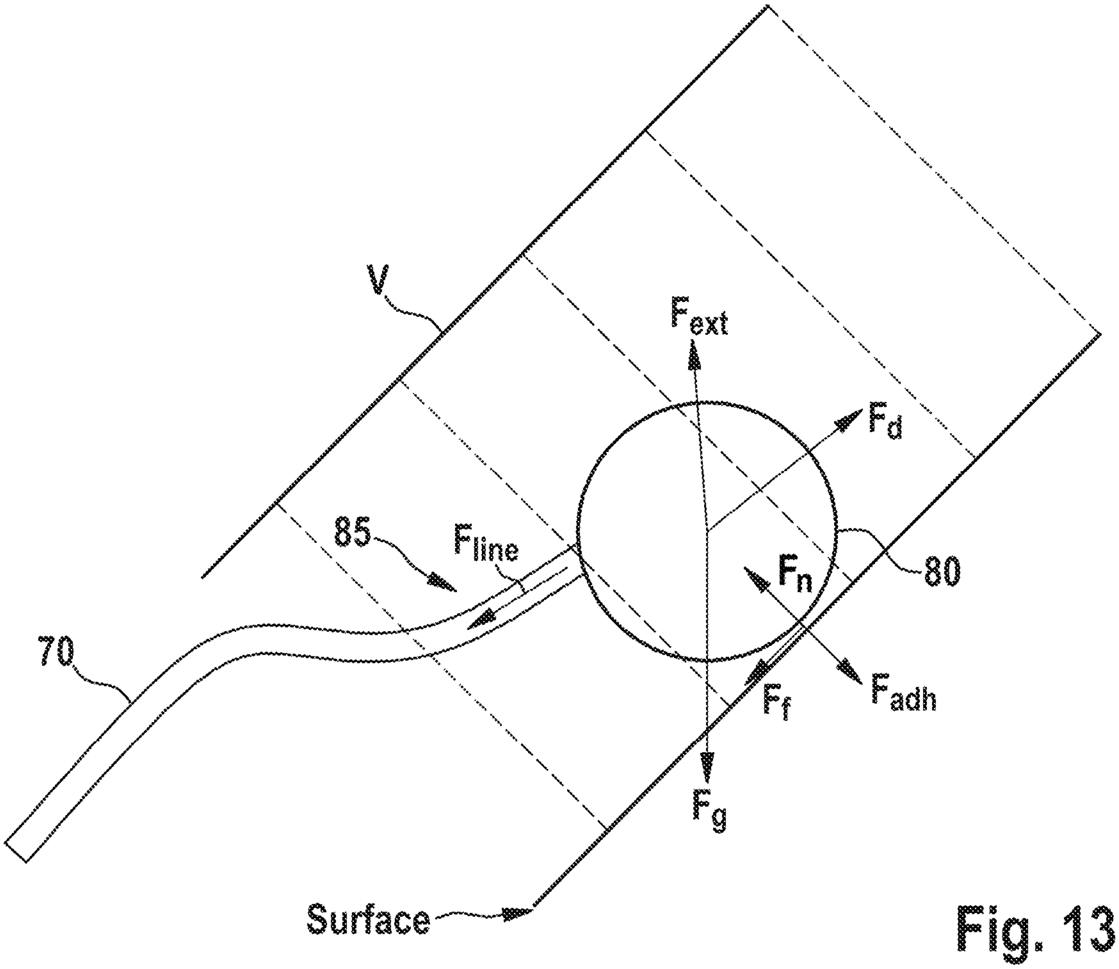

FIG. 13: a schematic illustration of the forces acting on a medical device.

Figure 14B:
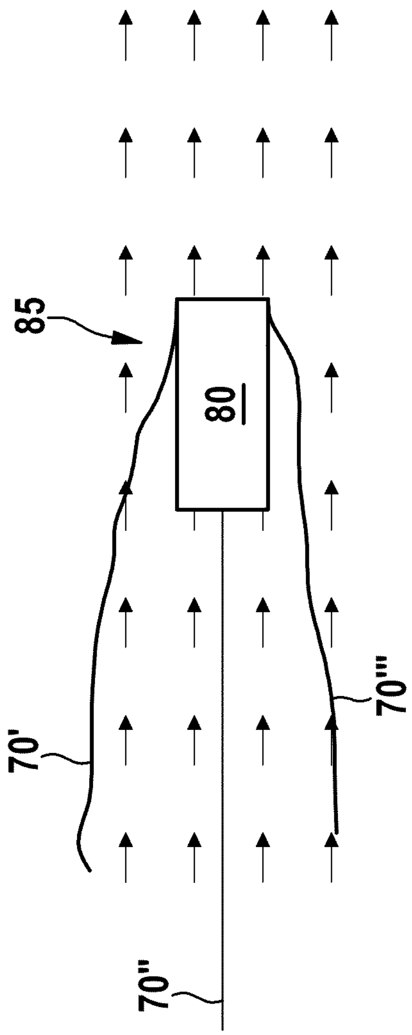
Figure 14C:
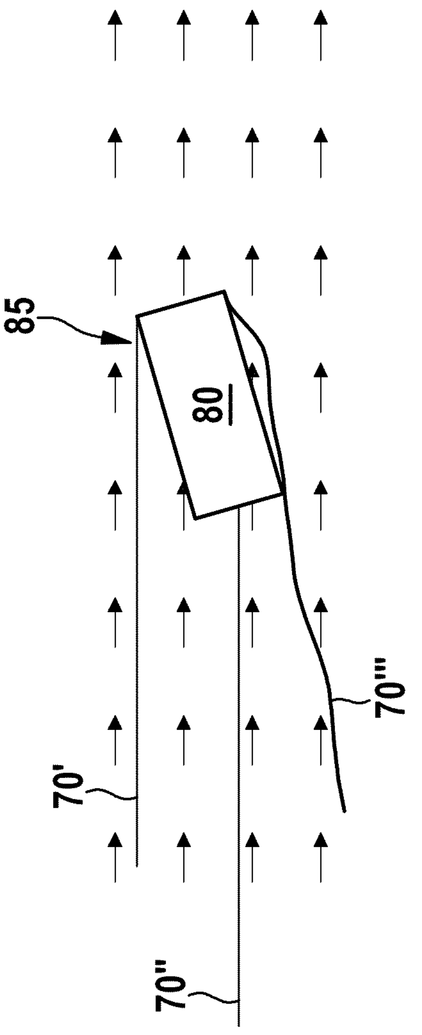
Figure 14A:
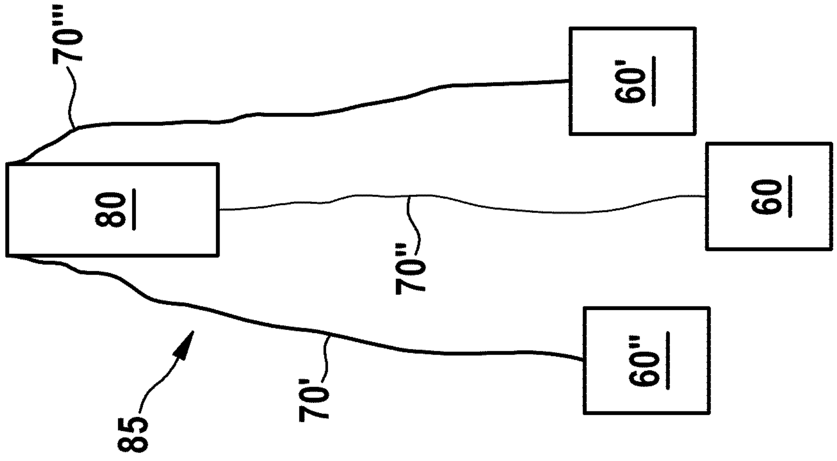

FIGS. 14*a*-14*c*: schematically a medical device with three controlling lines.

Figure 15B:
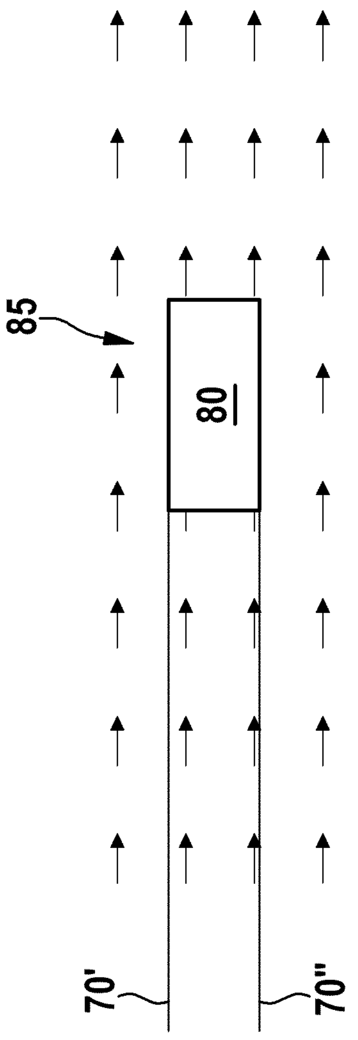
Figure 15C:
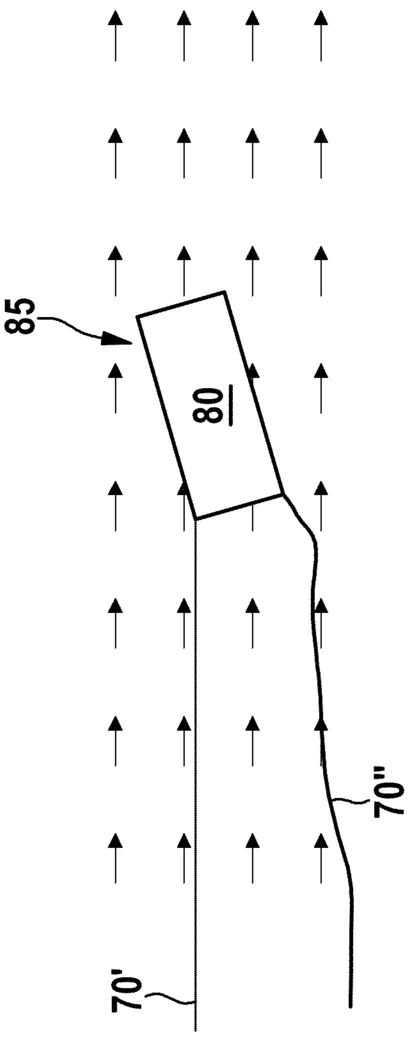
Figure 15A:
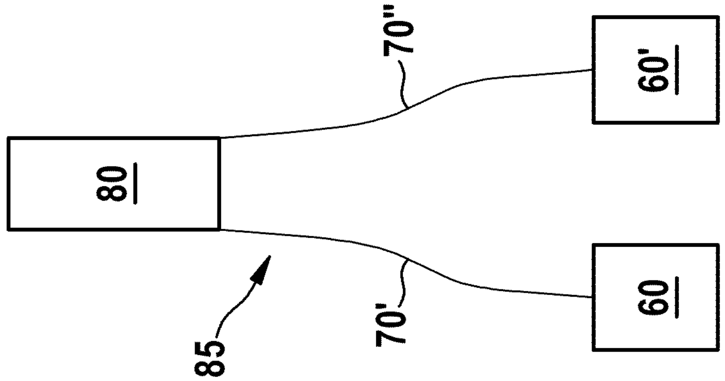

FIGS. 15*a*-15*c*: schematically a medical device with two controlling lines.

Figure 16A:
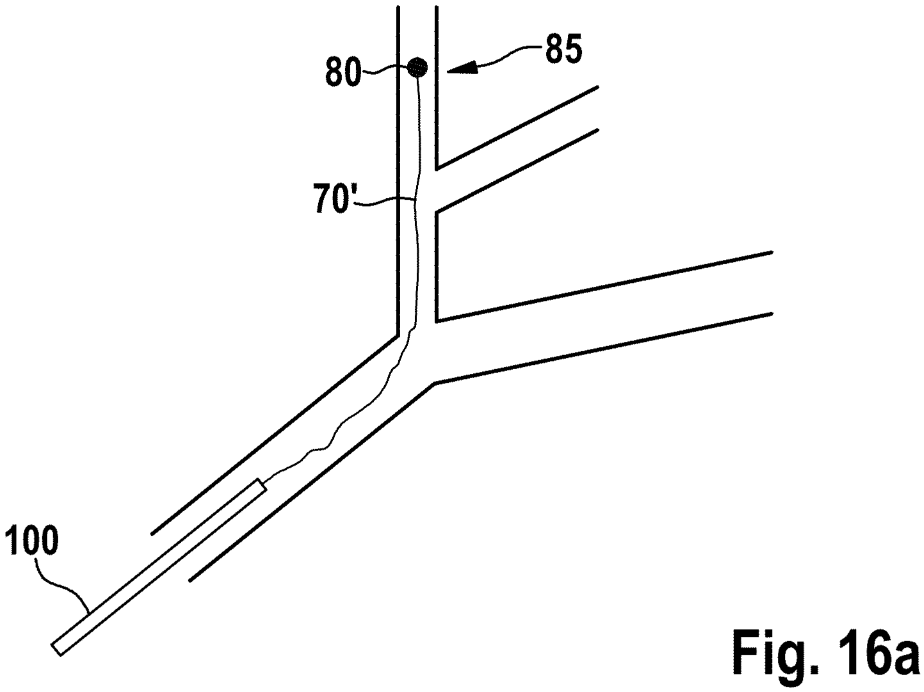
Figure 16B:
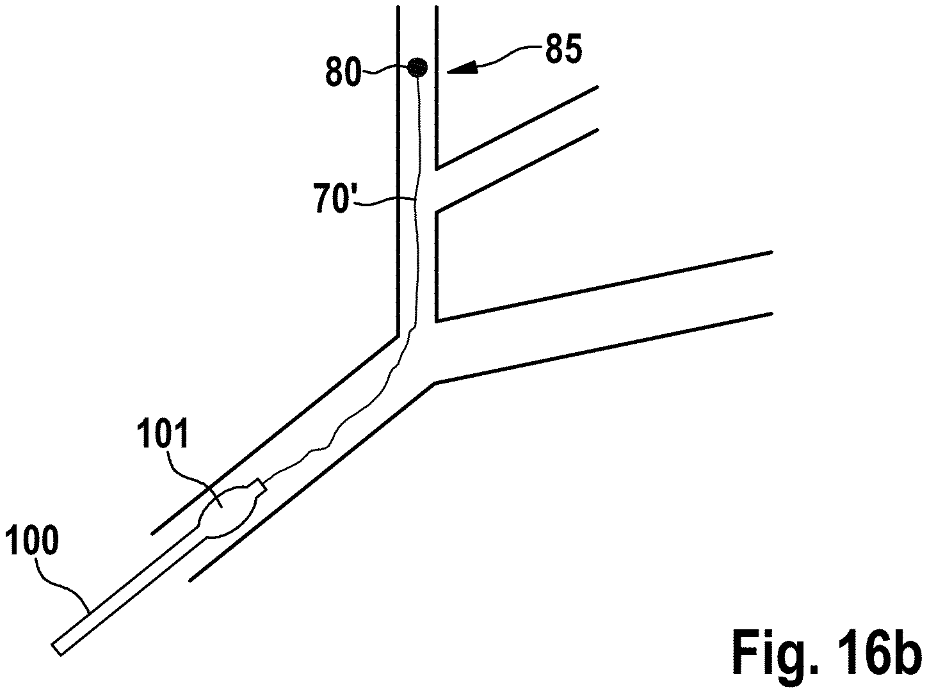

FIG. 16*a*-16*b*: schematically a system including a medical device and an additional device to influence blood flow in a vessel.

Figure 17A:
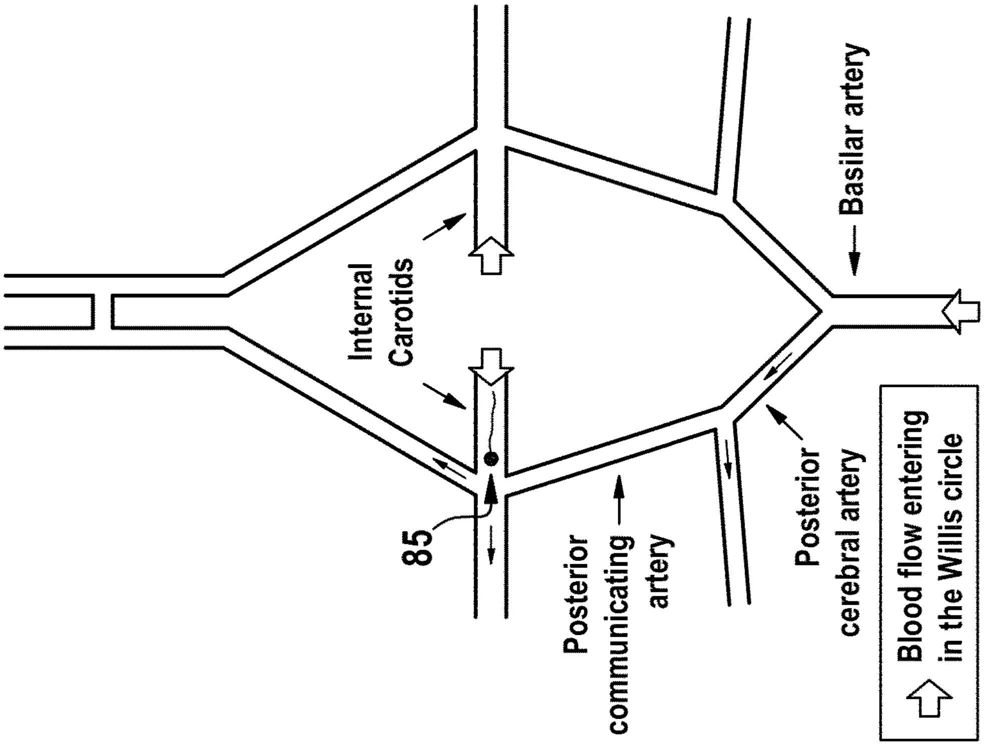
Figure 17B:
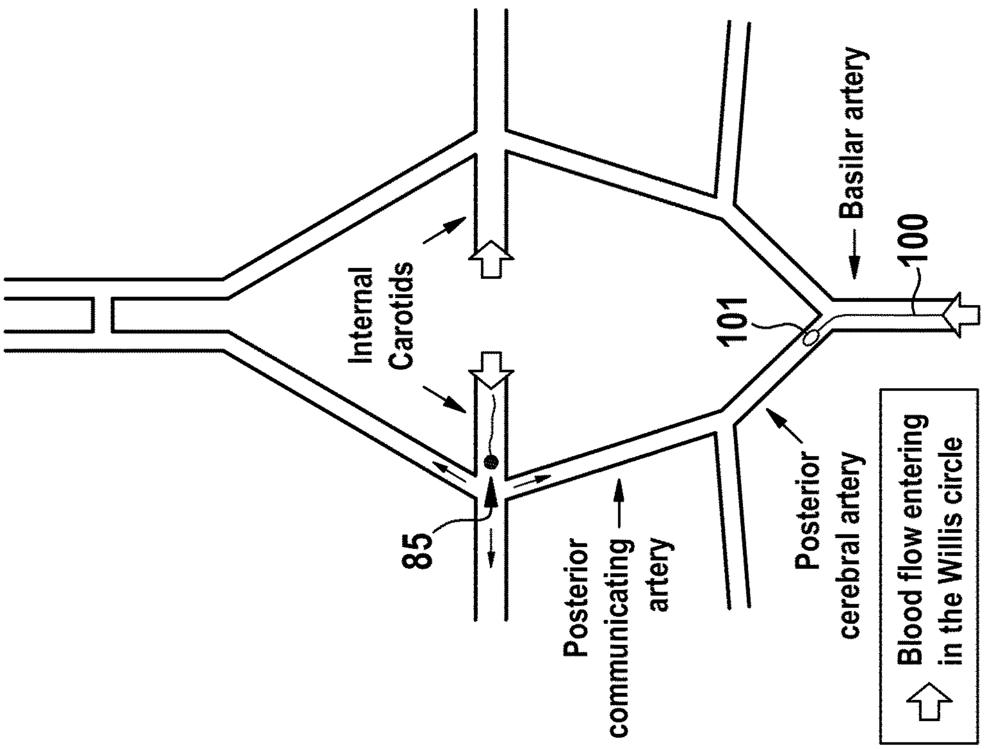

FIG. 17*a*-17*b*: schematically an alternative system with a medical device and a device to influence blood flow in a vessel.

Figure 18:
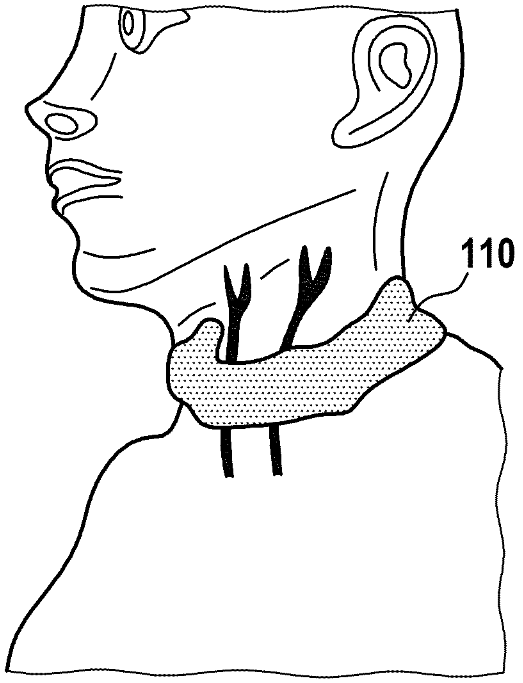

FIG. 18: schematically an alternative device to influence blood flow in a vessel.

FIG. 1 a shows an embodiment of a controlling line driver 60. The controlling line driver 60 comprises and electric motor 62 For clarity, a connection to a controlling unit (see FIG. 9) is omitted. It will be understood that the controlling unit may be connected to the controlling line driver 60 by any means known in the art, such as cables or wireless connections (such as Bluetooth, wireless local area network (LAN), infrared ports, or others). The controlling line driver 60 further comprises an axel 61 which is in operable connection with the electric motor 62. The axel is adapted to receive a controlling line 70, which can be rolled around the axel 61. Rotation of the axel 61 releases or pulls in the controlling line 70. The controlling line driver 60 further comprises a clamp 63. Here, the clamp 63 is shown in an open arrangement, allowing the controlling line 70 to move freely through the clamp. Thus, release, stop, or pull-in of the controlling line 70 is controlled only via the axel 61. Here, a medical device head section 80 is attached to the controlling line 70. The position of the medical device is controllable by the controlling line driver 60 and the axel 61 via movement of the controlling line 70.

Figure 1B:
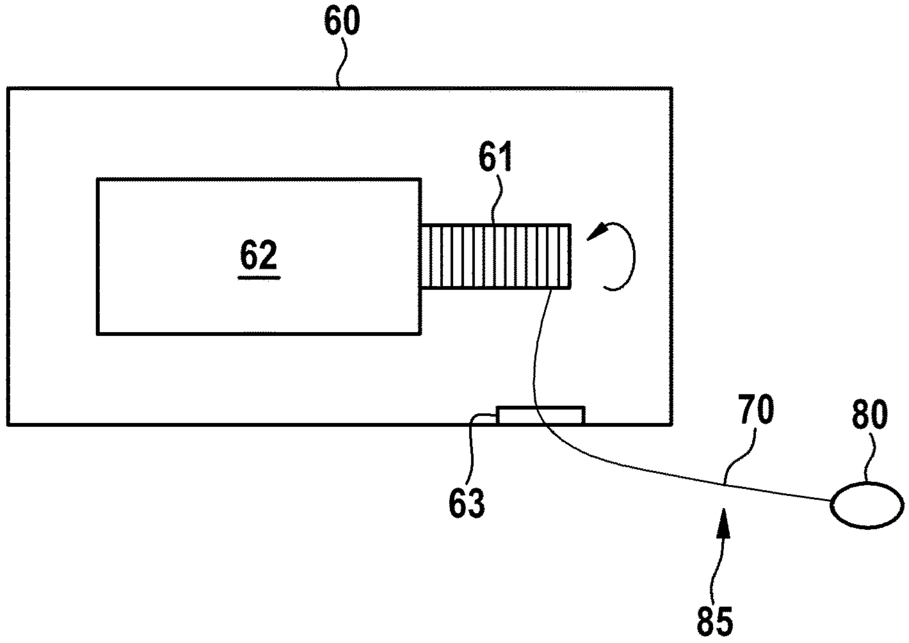

FIG. 1*b* shows the controlling line driver 60 of FIG. 1*a*, wherein the clamp 63 is shown in closed configuration. Thus, the controlling line 70 can be stopped and held independently of movement of the axel 61. For example, the medical device 85 may temporarily be held and secured without using power for the electric motor 62. Closing the clamp 63 to hold the controlling line 70 may also be advantageous to secure the medical device 85 via the controlling line in case of a malfunction of the controlling line driver 60. The clamp 64 may, however, be used to stop and/or hold the controlling line 70 at any time and for any reason.

Figure 1C:
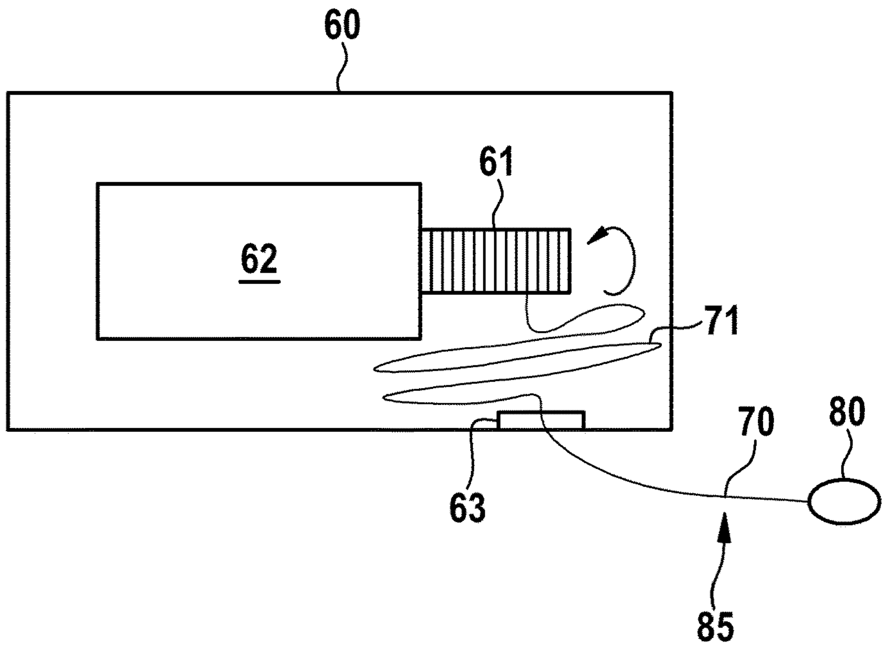

FIG. 1*c* shows the controlling line driver 60 of FIGS. 1*a* and 1*b*, wherein the controlling line 70 is released by rotation of the axel while the clamp 63 is closed. Thus, an accumulation 71 of controlling line forms within the controlling line driver 60 between the axel 61 and the clamp 63. Here, the clamp 63 is closed and the medical device 85 (via the controlling line 70) is held.

Figure 1D:
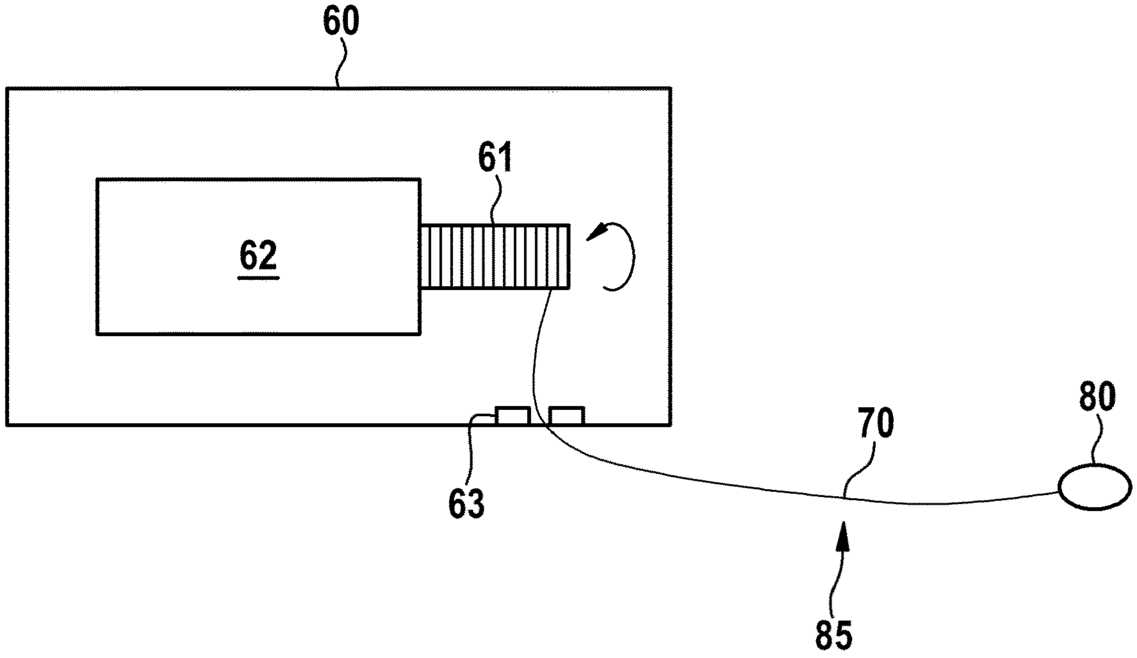

FIG. 1*d* shows the embodiment of FIGS. 1*a*-1*c*, wherein the clamp 63 is opened after the release of the controlling line within the controlling line driver 70 and the formation of an accumulation of controlling line as shown in FIG. 1*c*. Thus, the medical device 85 is allowed to flow substantially freely within a fluid such as blood until the controlling line 70 is extended as shown here. The method of operating a controlling line driver 60 as shown here is particularly advantageous to reduce tension in the controlling line 70 during navigation, for example if no bifurcations are to be navigated for a certain path. It will be understood that a force exerted on the medical device 85 by the controlling line 70 when navigated as shown in FIGS. 1*c* and 1*d* is temporarily substantially 0, and that a controlling unit (see FIG. 9) may balance the magnetic force with drag force accordingly.

Figure 2A:
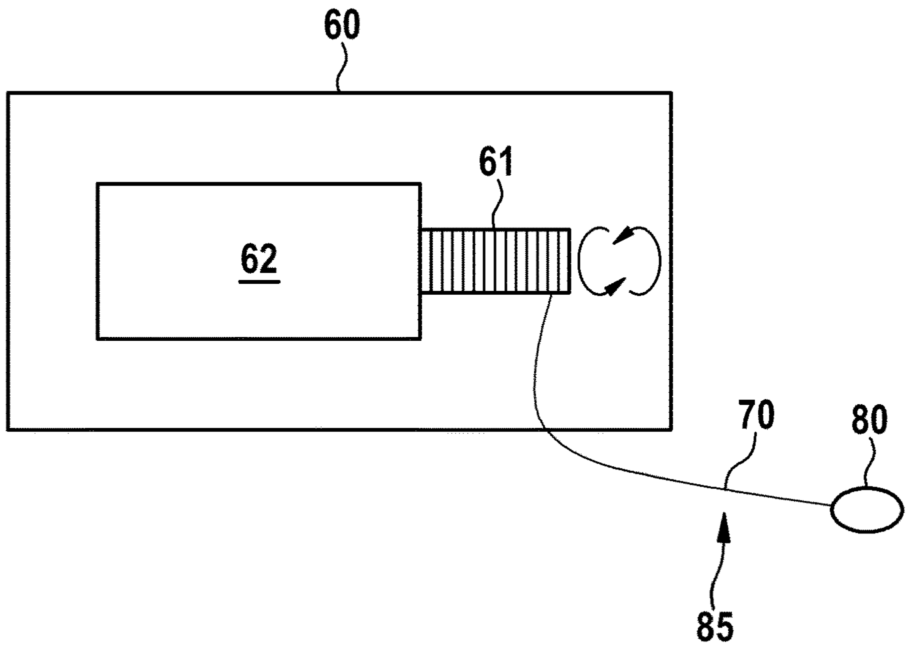

FIG. 2*a* shows a controlling line driver 60 that is substantially similar to the controlling line driver of FIGS. 1*a*-1*c*. However, in the present embodiment, no clamp (see FIG. 1*a*) is arranged. Thus, the velocity of the controlling line 70 may directly controlled by the axel 61. The medical device head section 80, when attached to the controlling line 70, thus moves at a maximum velocity controlled by the velocity of the controlling line 70 and the release velocity of the controlling line driver 70. Typically, a user may decide to navigate the medical device 85 at a velocity lower than the velocity of a blood flow surrounding that medical device. In such a case, the velocity of the medical device substantially corresponds to the release velocity of the controlling line 70 determined by the rotation speed of the axel and the electric motor 62. Thus, a controlling unit (see e.g. FIG. 9) may be employed to control the movement of the medical device 85 via control of the electric motor 62. It will be understood, however, that a user may also choose to release, via the controlling unit, the controlling line 70 at a faster speed than the velocity of the blood flow in order to move the medical device head section 80 at substantially the velocity of the blood flow.

Figure 2B:
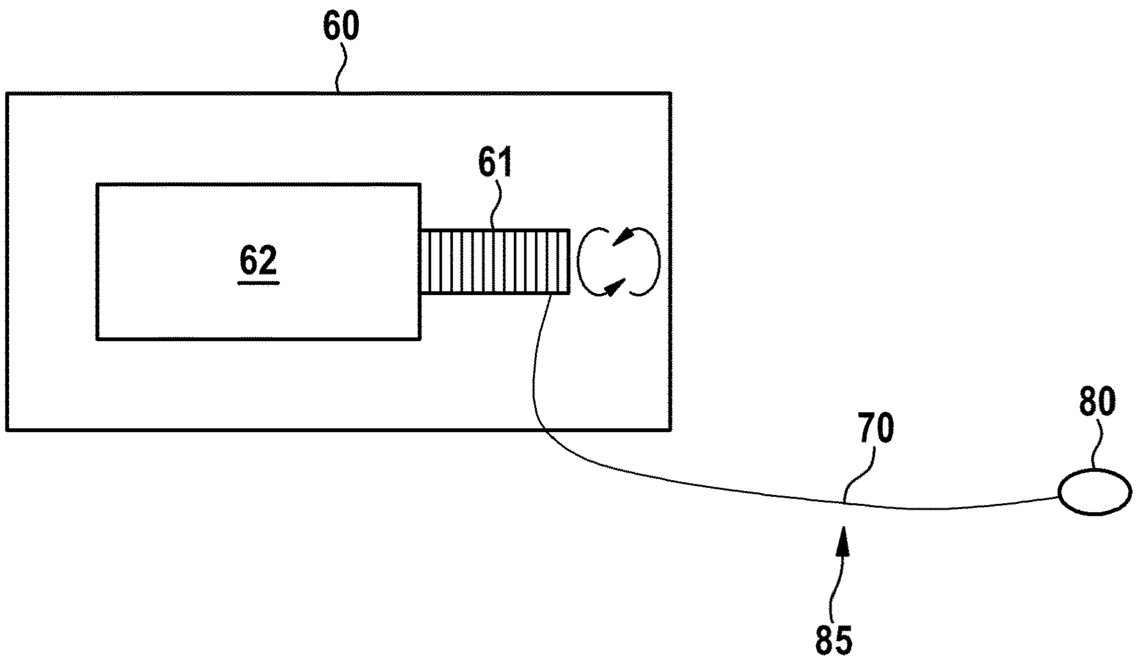

FIG. 2*b* shows the embodiment of FIG. 2*a* wherein the controlling line has been released further and the medical device 85 has moved downstream accordingly.

Figure 3A:
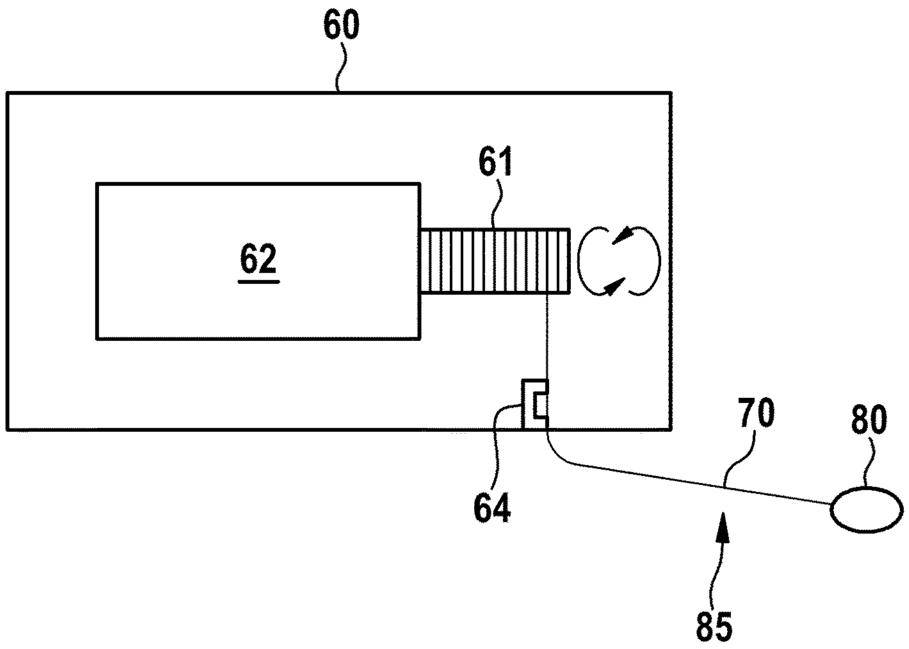

FIG. 3*a* shows a further embodiment of a controlling line driver 60. The embodiment shown here is similar to the embodiments shown in FIGS. 1-1*d* and FIGS. 2*a*-2*b*. In the present embodiment, the controlling line driver further comprises a force sensor 64 adapted to detect a pull force exerted on the controlling line and/or the medical device head section 80. When the medical device 85 is only surrounded by blood, for example, and has not encountered any obstacles, the medical device is typically substantially propelled by the drag force exerted by the blood, wherein the controlling line 70 may slow the medical device 85 down. Thus, the pull force measured by the force sensor 64 may provide a correlation with a drag force by the blood flow. It may thus be possible to calculate a drag force based on the release velocity of the controlling line 70 and the force measured by the force sensor 64.

Figure 3B:
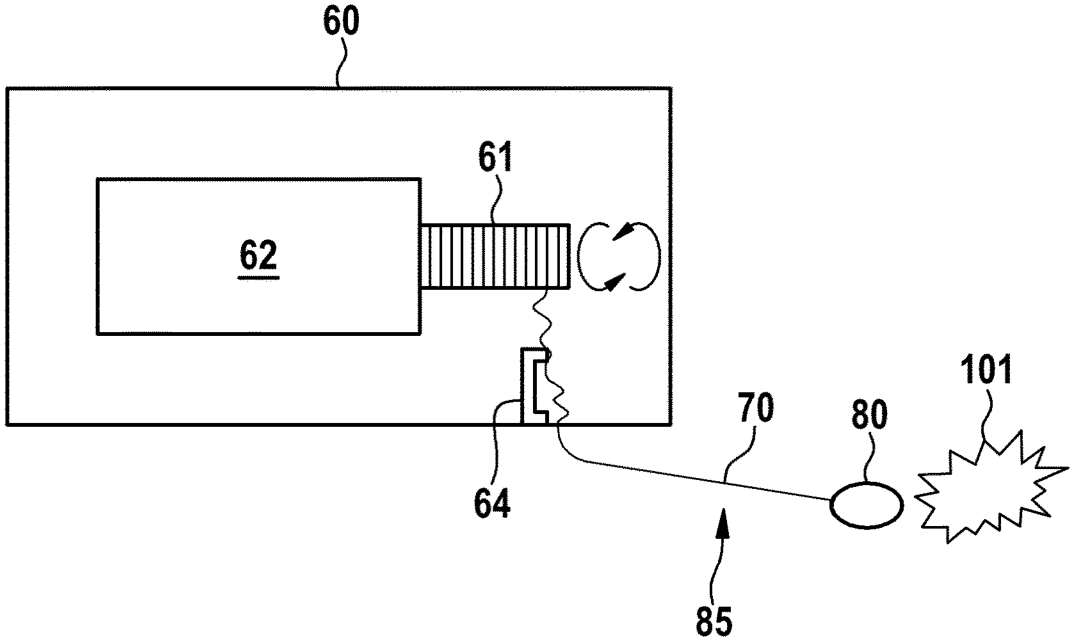

FIG. 3*b* shows the embodiment of FIG. 3*a*, wherein the medical device 85 has encountered an obstacle, here a thrombus 101. Thus, the movement of the medical device is slowed down, and a tension in the controlling line 70 is decreased. The force sensor 64 thus measures a lower force. On one hand, this allows to balance other forces as disclosed herein, for example to increase or decrease a magnetic force and/or the release velocity of the controlling line 70 accordingly. On the other hand, it may also be possible to detect obstacles 101 by analysis of the force data provided by the force sensor 164.

Additionally or alternatively, optical sensors may be used to monitor bending and/or a change in diameter and/or crosssectional area or shape of the controlling line 70, which may in turn be used to calculate a force acting on the controlling line 70 and/or the medical device head section 80.

Figure 4A:
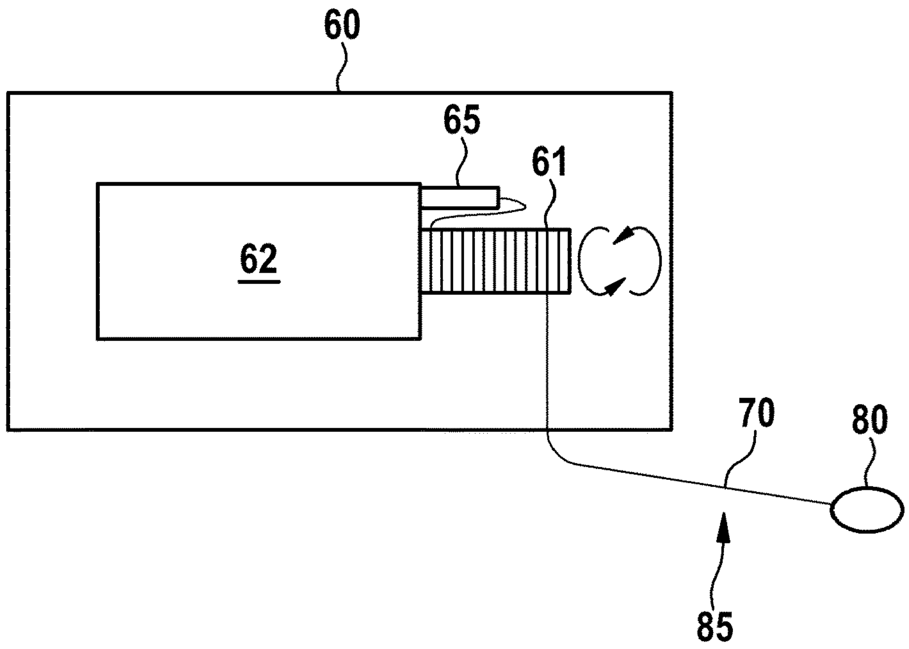

FIG. 4*a* shows a further embodiment of a controlling line driver which is similar to the embodiments of FIGS. 1*a*-1*d*, FIGS. 2*a*-2*b*, and FIGS. 3*a*-3*b*. Here, the controlling line driver 60 further comprises a trigger 65 adapted to trigger a function of the medical device head section 80 (and/or the medical device 85). Specifically, the trigger 65 may comprise optical fibers, fluid transmission tubes for liquids or gases, electrically conductive fibers or wires, or wireless signal transmission means.

Figure 4B:
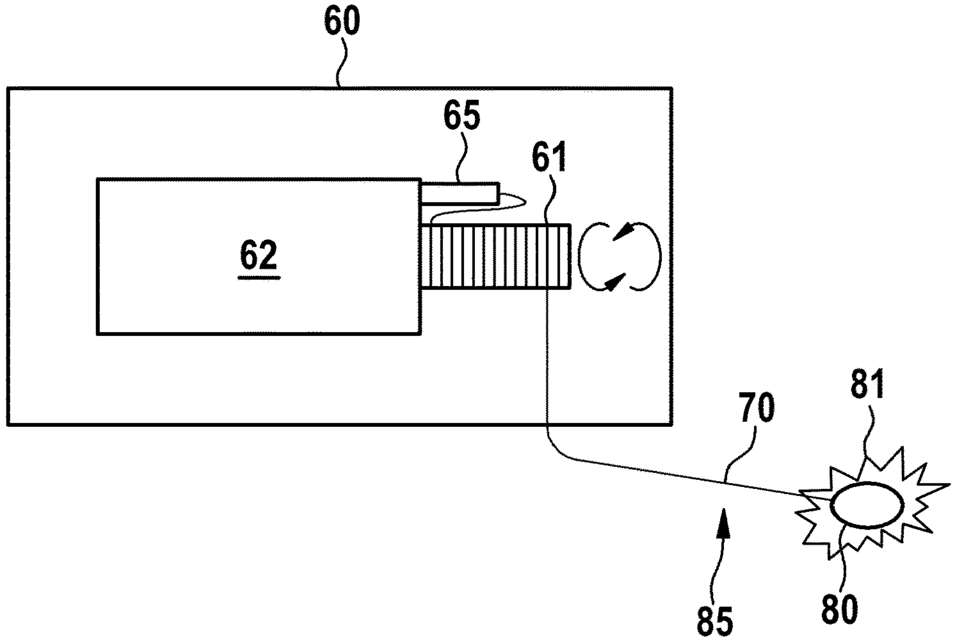

FIG. 4*b* shows the controlling line driver after the trigger 65 has stimulated the medical device 85 may perform an action 81, or example a release of a drug, mechanical removal, cutting, obliteration, heating, cooling, release of an adhesive, and/or inducement of thrombosis.

FIG. 5 shows a user interface 90 for a controlling unit (see FIG. 9). The user interface 90 has multiple screens 91, 92, 93, 94 showing treatment and/or navigation characteristics. Here, the interface 90 comprises a first screen 91 that shows a patients' vasculature V. The first screen 91 is configured as a touch screen and allows a user to define a target area G and/or a preferred trajectory T. Here, the target G was defined and the controlling unit has calculated automatically an optimal trajectory T. The trajectory is saved as data in a memory (not shown). A second subscreen 92 shows the vasculature with the position of the medical device 85. A third subscreen 93 shows controlling line driver parameters and provides an input interface by being configured as a touchscreen. When controlled automatically, the third subscreen may display actual values such as a rotation velocity, a device velocity and/or stimuli activation (see FIGS. 4*a*-4*b*). A user may, however, also set certain device velocity, wherein the controlling unit may determine other parameters (such as release velocity of the controlling line, magnetic forces, etc.) automatically to reach the desired value set by the user. A fourth subscreen 94 displays parameters of a magnetic actuator (see FIGS. 10*a*-10*c* and FIG. 11). Similar to the third subscreen, actual values may be displayed such that a user may monitor them. A user may also set certain values, if desired. Preferred values that can be displayed and/or set via the fourth subscreen are position and orientation in x-, y- and z-directions in space, displacement velocity of the magnetic actuator, and/or distance of the magnetic actuator to a patient. It will be understood that other parameters may be displayed or set in addition or as an alternative.

FIG. 6 shows a concept wherein a medical device 85 is moved in a vessel V in order to reach a target area G. Here, a blood drag force F2 and a magnetic force F1 act on the medical device. Thus, although the medical device 85 is moved generally in the direction of the magnetic force F1, the drag force F2 is strong enough to move the medical device to a second position 82 and subsequently to a third position which correspond to a vessel branch away from the target.

FIG. 7 shows a medical device 85 which is navigated by a system according to the invention. The medical device head section 80 is attached to a controlling line 70 which provides a third force F3 to the medical device, in addition the blood drag force F2 and the magnetic force F1. Because the system detects the drag force F2 (see, for example, FIGS. 3*a*-3*b*), the system may, via the controlling unit (see FIG. 9) balance and set the pull-back force F3 and the magnetic force F1 such that the total force acting on the medical device 85 moves the medical device to a second position 82 and subsequently to a third position 83 in the direction of a target area G.

FIG. 8 shows a system 10 according to the invention. The system comprises controlling unit 50, which is in operable connection with a magnetic actuator 40 and a controlling line driver 60. The controlling line driver 60 may, for example, be any controlling line driver 60 shown and described herein, and is connected to a controlling line 70. The controlling line 70 is inserted into a vessel of a patient P and holds a medical device head section 80. Here, the medical device 85 is guided to a head of the patient to treat a vessel in the brain.

FIG. 9 shows a system 10 according to the invention which is similar to the system of FIG. 8. In addition, the system shown here further comprises an imaging system 11. The imaging system may in particular be an ultrasound imaging system, a Doppler ultrasound imaging system, a fluoroscope, positron emission tomography (PET) scanner, computed tomography (CT) CT scanner, magnetic resonance imaging (MRI) system, or any other imaging system known in the art.

FIGS. 10*a*-10*c* schematically show different magnetic actuators 40 that may be used with any of the systems 10 described herein. The magnetic actuators 40 shown here comprise electromagnets. By means of the controlling unit (see FIGS. 8 and 9), the characteristics of the magnetic field 41 in order to create a magnetic force acting on the medical device at its position.

FIG. 10*a* shows the magnetic actuator 40, wherein the controlling unit controls the power and direction of electricity such that the strength of the magnetic field 41, here illustrated by the density and number of lines 41, is moderate. The magnetic field is oriented from up to down (symbolized by arrows) and may have a strength of up to 75 Millitesla. It will be understood that the magnetic field strength values shown herein are of exemplary nature and may of course be configured to any value, in particular values lower than the ones shown here.

FIG. 10*b* shows the magnetic actuator 40 of FIG. 10*a*, wherein the controlling unit is controlling the electromagnet such that the magnetic field strength is set to higher value, as compared to the embodiment of FIG. 10*a*, of 150 Millitesla (illustrated by the higher density of lines 8). The magnetic field direction is set from down to up.

FIG. 10*c*, shows the magnetic actuator 40 of FIGS. 10*a* and 10*b* is controlled by the controlling unit such that the magnetic field 41 has a strength of 75 millitesla and the direction of the magnetic field is oriented from down to up, i.e. in the same direction compared to FIG. 10*b* and opposite direction compared to FIG. 10*a*.

FIG. 11 shows an exemplary embodiment of a system 10 according to the invention. The system comprises a controlling unit 50 which is in operable connection with three magnetic actuators, 42, 43, 44 and four controlling line drivers 60, 60', 60", 60'". Each controlling line driver 60, 60', 60", 60'" is connected to one controlling line 70, 70', 70", 70'" each. Each controlling line 70, 70', 70", 70'" is in turn attached to a medical device head section 80, 80', 80", 80'". The controlling unit 50 is adapted to operate on several bifurcations B1, B2. Here, the vessel V is a carotid and comprises two bifurcations B1, B2 that into several branches V1, V1', V1", V2', V2". The four medical device head sections 80, 80', 80", 80'" each comprise a magnetic microparticle 84 for interaction with a magnetic field 41', 41", 41'". Two magnetic actuators 42, 44 are arranged such that they each create a magnetic field 41", 41'" with predefined characteristics at the first bifurcation B1. Here, the magnetic actuator 41 creates a magnetic field 41" that pushes the medical devices the branch V1'. By contrast, the magnetic actuator 44 creates a magnetic field 41'" that accelerates the moving elements into the branch V1". However, the magnetic actuators 42, 44 are configured to only create relatively weak magnetic field. By slowing down the medical device head sections 80, 80', 80", 80'" to a velocity lower than the blood flow velocity by means of the controlling line drivers 60, 60", 60'" and the controlling lines 70, 70', 70", 70'", the magnetic fields 41", 41'" are nevertheless sufficient to guide the medical devices toward the branch V1". The controlling unit 50 calculates the maximum velocity of the medical device head sections 80, 80', 80", 80'" such that the magnetic force exerted by the magnetic actuators 42, 44 is sufficient for guiding and controls the controlling line drivers 70, 70', 70", accordingly, such that the controlling lines are released at a corresponding speed. At the second bifurcation B2, another magnetic actuator 43 creates a magnetic field 41' that is adapted to move the medical device head sections 80, 80', 80", toward the branch V2' and away from the branch V2". The system 10 shown here enables to navigate medical device head sections 80, 80', 80", 80'" along a path that is complex and would not be accessible by passive moving and/or magnetic guiding with two forces as known in the art.

FIG. 12 schematically shows a possible working principle of a controlling unit according to the invention when it comprises a feedback loop. A part of the body of a patient P is imaged by an imaging unit 11. The controlling unit 50 is adapted to analyze the images, for example to determine the position of the moving element with respect to a bifurcation. Based on that information, the controlling unit 50 controls the magnetic field and/or the controlling line, in particular by moving and/or powering a magnetic actuator and/or controlling the controlling line driver, such as to guide the medical device depending on a desired trajectory. This process can be repeated multiple times if necessary.

FIG. 13 schematically illustrates a force balancing model which may be used to with a device and system according to the invention. A medical device 85 is shown in a vessel including a controlling line 70. The forces acting on the medical device 85 are:

Hydrodynamic force $F_d$
Gravitational force $F_g$
Adhesion force $F_{adh}$
Friction force $F_f$
Normal contact force on the surface $F_n$
Magnetic force $F_{ext}$
Force $F_{line}$ exerted by the controlling line 70

The hydrodynamic force $F_d$, the gravitational force $F_g$, and the adhesion force $F_{adh}$, Friction force $F_f$ and the normal contact force on the surface $F_n$ are forces that occur inherently when a medical device 85 is immersed in a blood stream. The magnetic force $F_{ext}$ and the force $F_{line}$ exerted by the controlling line 70 are artificially exerted and controlled by the system according to the invention.

The combination of the different forces described above determines the speed vector (orientation & intensity) and therefore the movement of the medical device 85 in the vessel V.

The motion of the medical device 85 may be described using the following equation (where m is the mass of the medical device and $v_r$ its velocity):

$$m\frac{dv_r}{dt} = F_g + F_d + F_n + F_{line} + F_f + F_{adh} + F_{ext}$$

The purpose of the force balancing is to determine necessary forces to be exerted by the system that, combined with the naturally occurring forces will generate a speed vector suitable to move the medical device 85 along a pre-determined trajectory.

In particular, the force balancing as described above allows to stop, to pull back, to take a bifurcation and/or to steer the medical device 85 in a vessel with reduced flow.

The different forces can be pre-determined, estimated, measured directly, measured indirectly, or neglected.

To illustrate the above, two exemplary calculations using the above model are shown. Two sizes of medical devices (1.2 mm and 0.6 mm) are modelled for two different bifurcations (internal carotid artery segment 1, hereinforth ICA1-R, to internal carotid artery segment 2, hereinforth ICA2; and ICA2 to anterior cerebral artery segment 1, hereinforth ACA1):

A medical device head section 80 with a size of 1.2 mm would need to be subjected to a magnetic force of $2.9\cdot10^{-6}$ N by a magnetic actuator having a volume of 400 cm 3 and which is placed at a distance of 45 cm to pass the ICA1-R to ICA2 bifurcation. To pass the ICA2 to ACA1 bifurcation, a force of $8.9\cdot10^{-5}$ N and a distance of 17 cm is necessary.

Similar calculations for a medical device head section 80 with a size of 0.6 mm yield $3.7\cdot10^{-6}$ N at a distance of 24 cm (ICA1-R to ICA2) and $5.4\cdot10^{-5}$ N at a distance of 10 cm (ICA2 to ACA1).

The equation shown above allows to estimate the acceleration (i.e. speed variation) of a medical device taking into the different forces acting on it.

Typically, all force acting on the device 80 are known except the force $F_{line}$ of the controlling line 70. Thus, the force balance equation may be solved by either one of two ways:

- estimate the force exerted by the controlling line 70 and compute the acceleration of the medical device 85
- determine the acceleration of the medical device and compute the resulting force exerted by the controlling line 70.

There is an equivalence between the acceleration of the medical device head section 80 and the force exerted by the controlling line force 70. It is possible to determine force exerted by the controlling line 70 from the acceleration of the medical device 85 or to determine the acceleration of the medical device head section 80 from the force exerted by the controlling line 70.

For example, in one configuration of the system, the speed or the acceleration of the medical device can be controlled by controlling the speed at which the controlling line driver (not shown) releases the controlling line 70. The force exerted by the controlling line 70 can be determined from the speed/acceleration of the medical device.

FIGS. 14 *a*-15 *c* show different embodiments of medical device 85 with several controlling lines 70', 70", 70".

FIG. 14*a* shows an embodiment of a medical device 85 with three controlling lines 70', 70", 70'". Each controlling line 70', 70", 70'" is attached to a controlling line driver 60, 60', 60" and may be controlled independently. The controlling line drivers may be independent or integrated in one unit.

FIG. 14*b* shows the medical device 85 of FIG. 14*a* in a fluid stream (e.g. blood). Here, the medical device 85 is intended to flow substantially straight and with the fluid flow. Accordingly, all three controlling lines 70', 70", 70'" exerted the same force on the medical device 80.

FIG. 14 *c* shows the medical device 85 of FIGS. 14 *a*-14 *b* during a steering motion. Here, the controlling line 70" has been loosened while controlling lines 70', 70" still exert a force on the medical device head section 80. As a consequence, the medical device 85 is steered in the direction of controlling lines 70', 70".

In the shown embodiment, the medical device is attached to three controlling lines 70', 70", 70'" that can be independently activated by the controlling line driver (not shown). By adjusting the tension of the different controlling lines, the system may modify the position of the medical device in the blood stream and may change the forces acting on it.

This control can help to balance the forces acting on the medical device 85 such as to orient the medical device toward the flow stream leading to the targeted artery.

The tension or the force on the different controlling lines 70', 70", 70'" can be controlled by the release/rewind speed/movement of the different controlling lines.

FIG. 15*a* shows and alternative embodiment of a medical device which is similar to the embodiment of FIGS. 14*a*-14*c*. Here, only two controlling lines 70', 70" are attached to the medical device head section 80. Each controlling line 70', 70" is attached to a controlling line driver 60, 60' and may be controlled independently.

FIG. 15*b* shows the medical device 85 in a blood stream flowing substantially with the blood stream. Both controlling lines 70', 70" exert substantially the same force on the medical device 85.

FIG. 15 *c* shows the medical device 85 of FIG. 15 *b* wherein the controlling line 70" has been loosened such as to steer the medical device 85 substantially as described in the context of FIG. 13 *c*.

It will be understood that any number of controlling lines may be used depending on the intended application. The embodiments shown in FIGS. 14 and 15 with three and two controlling lines, respectively, are of exemplary nature.

In general, a higher number of controlling lines may be advantageous as it allows for more versatile and precise steering. By contrast, fewer controlling lines may allow for easier and cheaper manufacturing and easier operation of the medical device.

It is conceivable that one or more controlling lines are configured to be rotatable, in particular such as to rotate the medical device. Preferably, several or all controlling lines would be rotatable around the same axis.

Additionally or alternatively, at least two controlling lines may be configured as a spiral, in particular an elastic spiral. Thus, a rotation of the medical device may be induced by the controlling lines. The controlling lines, due to the spiral shape, may exert a torque on the medical device. A release mechanism may be used to release the spiraled controlling lines.

It is also conceivable that one or multiple lines are adapted to pick up and/or release a ballast. For example, a chamber may be adapted to be opened or closed via the controlling line. A ballast, for example saline, may be released by opening the closed chamber. It is also conceivable that the closed chamber contains gas or vacuum and opening it causes picking up of blood, thus increasing the weight of the medical device. In particular, a nitinol spring may be used to open and/or close the chamber. FIG. 16*a* shows a catheter device 100 used to deliver a medical device 85 to a general area to be treated. The medical device head section 80 is attached to a controlling line 70 and may be navigated by any means described herein.

FIG. 16*b* shows the catheter device of FIG. 16*a*. Here, a balloon 101 attached to the catheter device 100 and arranged at its distal end has been inflated such as to limit the blood flow through the vessel to be treated.

It will be understood that such a balloon may be used optionally with any of the medical devices 85 disclosed herein. Furthermore, additionally or alternatively, any other means to control and/or limit blood flow may be used, for example other inflatable means, drugs, patient orientation, and/or a contention system. A patient may be oriented appropriated and stabilized using a pillow, for example.

A contention system may in particular be understood as a system that is adapted to apply a pressure to a patient's skin. The pressure is adapted to compress an artery such as to modify blood flow, in particular reducing or stopping the blood flow.

FIG. 17*a* shows schematically a medical device navigating the Willis circle trough an internal carotid. In general, it may be challenging to navigate a medical device in the posterior communicating artery from the internal carotid as the blood flow is generally low in the posterior communicating artery due to incoming flow from the posterior cerebral artery.

FIG. 17*b* shows the medical device substantially in the same position as shown in FIG. 17*a*. In order to reduce to flow in the posterior cerebral artery and to increase the flow in the posterior communicating artery, a second medical device 100, which is configured here as a medical device substantially as described herein and additionally comprises an inflatable balloon 101, is introduced in the posterior cerebral artery to temporarily reduce the blood flow. It will be understood that the second medical device may additionally or alternatively comprise or be formed by a catheter device.

Blocking or decreasing the blood flow in the posterior cerebral artery can increase blood flow from the carotid artery to the posterior communicating artery and can facilitate the navigation of the medical device.

It will be understood that a system according to the invention may thus comprises a device for reducing or controlling blood flow which is integrated in the medical device 85 and/or catheter device 100 for delivery, or configured as a separate part of the system which may be deployed entirely independently from the medical device 85.

FIG. 18 shows an alternative embodiment of a device 110 to reduce and/or control blood flow configured as a neck contention device. The device 110 is configured to compress the carotids to reduce the blood flow therein. Here, the compression device 110 is configured as a flexible ring attachable around the neck of a patient. In the internal side, the ring is divided into flexible parts which are activatable to compress the tissue underneath it. For example, mechanical compression may be achieved by inflating a balloon or using a micro-actuator.

The invention claimed is:

1. A system for moving, in a vascular network, a medical device including a magnetic part in a head section and a controlling line in a back section, the system comprising:

a magnetic actuator;

a controlling unit;

a controlling line driver;

wherein the controlling line driver is adapted to hold and/or to release at different speeds the controlling line when the controlling line is attached to the controlling line driver, wherein the magnetic actuator is adapted to generate a magnetic field at a location in order to pull the medical device, wherein the controlling unit is adapted to balance at least three forces applied on the medical device, the at least three forces comprising a flow drag force and a force acting on the medical device through the controlling line, wherein the controlling unit is adapted to operate at least one of the magnetic actuator and/or the controlling line driver, and wherein the controlling unit is adapted to compute the at least three forces based on trajectory data that are representative for a predetermined vascular path.

2. The system according to claim 1, wherein the controlling unit is adapted to balance at least four forces applied on the medical device.

3. The system according to claim 1, wherein the controlling unit is adapted to take into account a friction force induced by the controlling line with a vessel wall of the vascular network.

4. The system according to claim 1, wherein the controlling unit is adapted to balance the contact forces induced by the head section with a vessel wall of the vascular network.

5. The system according to claim 1, wherein the system comprises at least two magnetic actuators and wherein the controlling unit is adapted to control the at least two magnetic actuators.

6. The system according to claim 1, wherein the controlling unit has an interface for receiving intraoperative data from an imaging system, wherein the controlling unit is adapted to locate the position of the medical device.

7. The system according to claim 1, wherein the controlling unit has an interface for the user to enter the trajectory data.

8. The system according to claim 1, wherein the controlling unit is adapted to control the controlling line driver to slow down and/or to stop the displacement of the medical device when moving at least one magnetic actuator to a next position.

9. The system according to claim 1, wherein the controlling line driver comprises a force sensor.

10. The system according to claim 1, wherein the controlling line driver comprises at least one interface to trigger and/or power at least one function of the medical device.

11. The system according to claim 1, wherein the controlling line driver and/or the controlling line is embedded into a sterile feature.

12. The system according to claim 1, comprising multiple controlling line drivers, wherein the controlling unit is adapted to operate the magnetic actuator and the multiple controlling line drivers to control the navigation of multiple medical devices.

13. The system according to claim 1, further comprising means for controlling and/or reducing blood flow in a vessel.

14. The system according to claim 1, comprising at least two controlling line drivers wherein the controlling unit is adapted to independently control the at least two controlling line drivers.

15. A method of treating or diagnosing a patient, comprising the steps of introducing a medical device in a vessel of a patient;

computing balanced forces applied on the medical device to create a resulting force able to move the medical device along a pre-determined path, wherein the balanced forces comprise at least a flow drag force and a force acting on the medical device through a controlling line;

operating least one magnetic actuator to create at least one magnetic field at at least one pre-determined location; and adapting a releasing velocity of a controlling line attached to the medical device.

16. The method according to claim 15, comprising the further steps of stopping the medical device prior to a bifurcation.

* * * * *